(12) United States Patent
Frey et al.

(10) Patent No.: US 8,906,979 B2
(45) Date of Patent: Dec. 9, 2014

(54) MACROPHOTOINITIATORS

(75) Inventors: Markus Frey, Rheinfelden (CH);
Christophe Frossard, Granges-Paccot (CH); Katia Studer, Rixheim (FR);
Bruno Spony, Wahlbach (FR); Patrizia Sgambati, Rheinfelden (DE)

(73) Assignee: BASF SE, Ludwigshafen (DE)

( * ) Notice: Subject to any disclaimer, the term of this patent is extended or adjusted under 35 U.S.C. 154(b) by 70 days.

(21) Appl. No.: 13/386,954

(22) PCT Filed: Jul. 26, 2010

(86) PCT No.: PCT/EP2010/060764
§ 371 (c)(1),
(2), (4) Date: Mar. 22, 2012

(87) PCT Pub. No.: WO2011/012560
PCT Pub. Date: Feb. 3, 2011

(65) Prior Publication Data
US 2012/0178844 A1    Jul. 12, 2012

(30) Foreign Application Priority Data
Jul. 30, 2009  (EP) ..................... 09166799

(51) Int. Cl.
*G03F 7/031* (2006.01)
*C08F 2/46* (2006.01)
*C07C 221/00* (2006.01)
*C07C 67/00* (2006.01)
*C07C 225/10* (2006.01)
*C07C 69/00* (2006.01)
*C07C 217/36* (2006.01)
*C07C 219/06* (2006.01)
*C08F 2/50* (2006.01)

(52) U.S. Cl.
CPC ............. *C07C 217/36* (2013.01); *C07C 219/06* (2013.01); *C08F 2/50* (2013.01); *G03F 7/031* (2013.01)
USPC ................. 522/8; 522/36; 564/328; 560/194; 252/182.26

(58) Field of Classification Search
USPC ......................... 522/8, 36; 564/328; 560/194; 252/182.26
See application file for complete search history.

(56) References Cited

U.S. PATENT DOCUMENTS

| | | | |
|---|---|---|---|
| 3,474,071 A * | 10/1969 | Byers et al. ................. | 525/430 |
| 3,844,916 A | 10/1974 | Gaske | |
| 4,218,218 A | 8/1980 | Daubach et al. | |
| 4,287,039 A | 9/1981 | Buethe et al. | |
| 4,339,566 A | 7/1982 | Rosenkranz et al. | |
| 4,376,788 A | 3/1983 | Montanari | |
| 4,384,056 A | 5/1983 | Schmidt et al. | |
| 4,575,330 A | 3/1986 | Hull | |
| 4,753,817 A | 6/1988 | Meixner et al. | |
| 5,013,768 A | 5/1991 | Kiriyama et al. | |
| 5,186,846 A | 2/1993 | Brueckmann et al. | |
| 5,482,649 A | 1/1996 | Meixner et al. | |
| 5,538,548 A | 7/1996 | Yamazaki | |
| 5,587,404 A | 12/1996 | Kroner et al. | |
| 5,620,751 A | 4/1997 | Brindoepke et al. | |
| 5,734,002 A | 3/1998 | Reich et al. | |
| 5,922,473 A | 7/1999 | Muthiah et al. | |
| 6,294,592 B1 | 9/2001 | Herrmann et al. | |
| 6,306,555 B1 | 10/2001 | Schulz et al. | |
| 2010/0274012 A1 | 10/2010 | Guire | |

FOREIGN PATENT DOCUMENTS

| | | |
|---|---|---|
| AU | 2598071 | 9/1972 |
| DE | 2116213 | 11/1971 |
| DE | 2936039 | 4/1981 |
| DE | 4228514 | 3/1994 |
| DE | 19700064 | 7/1997 |
| DE | 19727767 | 1/1999 |
| EP | 0012339 | 6/1980 |
| EP | 0033896 | 8/1981 |
| EP | 0041125 | 12/1981 |
| EP | 0126541 | 11/1984 |
| EP | 0245639 | 11/1987 |
| EP | 0279475 A | 8/1988 |
| EP | 0280222 | 8/1988 |
| EP | 0339841 | 11/1989 |
| EP | 0389427 A | 9/1990 |
| EP | 0438123 | 7/1991 |
| EP | 0636669 | 2/1995 |
| EP | 0678534 | 10/1995 |
| EP | 0704469 | 4/1996 |
| FR | 2092041 A | 1/1972 |
| GB | 2180358 | 3/1987 |
| GB | 2403478 | 1/2005 |
| JP | 56-128742 | 10/1981 |
| JP | 11-279523 | 10/1999 |
| WO | 9903930 | 1/1999 |
| WO | 0010974 | 3/2000 |
| WO | 0020517 | 4/2000 |
| WO | 0142313 | 6/2001 |
| WO | 2004074328 | 9/2004 |
| WO | 2006008251 | 1/2006 |
| WO | 2006/135910 A | 12/2006 |

OTHER PUBLICATIONS

Xiao et al., Polymbers for Advanced Technologies, No. 19, pp. 1305-1310 Jun. 9, 2008.

(Continued)

*Primary Examiner* — Michael Pepitone
*Assistant Examiner* — Jessica Roswell
(74) *Attorney, Agent, or Firm* — Shruti Costales

(57) ABSTRACT

The invention pertains to high-molecular photoinitiator compounds comprising a photoactive moiety Q and an amine functionality, preferably a tertiary amino group, where the photoactive moiety Q is a benzoyl photoactive moiety.

7 Claims, No Drawings

(56) References Cited

OTHER PUBLICATIONS

Burrows, R. et al., "Multifunctional photoinitiators (MFPIs): A new concept", Surface Coatings International, Part B: Coatings Transactions, 2004, vol. 87, B2, pp. 127-135.

Houben-Weyl, Methoden der organischen Chemie, Georg Thieme Verlag, Stuttgart, vol. VI/3, pp. 465 (1965), vol. XI/1, pp. 311 (1957), vol. E16d, pp. 1202 (1992).

Ullmann's Encyclopedia of Industrial Chemistry, VCH Verlagsgesellschaft, Weinheim, 1991, 5th Ed., vol. A18, pp. 386-426.

Ullmann's Encyclopedia of Industrial Chemistry, VCH Verlagsgesellschaft, Weinheim, 1991, 5th Ed., vol. A18, p. 469.

Ullmann's Encyclopedia of Industrial Chemistry, VCH Verlagsgesellschaft, Weinheim, 1991, 5th Ed., vol. A18, pp. 404-407.

Ullmann's Encyclopedia of Industrial Chemistry, VCH Verlagsgesellschaft, Weinheim, 1991, 5th Ed., vol. A18, pp. 491-500.

Bielemann, J., Lackadditive, Wiley-VCH Verlag. GmbH, Weinheim, 1998, pp. 244-247.

Wittig, M. et al., "Radiation Curing of Powder Coating: a possibility for powder coating to enter new application areas", Conference Proceedings, Radtech Europe, 1993, pp. 533-545.

Nishimura, I. et al., "Synthesis of Self-Photosensitizing Polyesters Carrying Pendant Norbornadiene (NBD) Moieties and Benzophenone Groups and Their Photochemical Reactions", Macromolecules 1998, vol. 31, 2789-2796.

English language machine-generated translation of DE19700064 (12 pages); 1997.

English language machine-generated translation of EP0033896 (10 pages); 1981.

English language machine-generated translation of EP0280222 (11 pages); 1988.

English language machine-generated translation of EP0704469 (11 pages); 1996.

English language machine-generated translation of JP11-279523 (7 pages); 1999.

\* cited by examiner

MACROPHOTOINITIATORS

The invention pertains to novel high-molecular photoinitiators, a process for their preparation as well as the use in photopolymerizable compositions.

In the art ring-opening addition reactions of glycidoxylated benzophenone to amine compounds are described. For example in U.S. Pat. No. 3,474,071 the ring-opening addition of glycidoxylated benzophenone to amine terminated polycarbonamide (Nylon) of MW 10'000 and higher is described. GB2403478 discloses the Michael addition of piperazinyl-benzophenone to oligoacrylates. In Surface Coatings International, Part B: Coatings Transactions 2004, 87(B2), 127-135 the Michael addition of acryloylated 2-hydroxy-1-[4-(2-hydroxyethoxy)phenyl]-2-methyl-1-propanone to diamines is presented.

There is a need for photoinitiator compounds providing a good reacitivty profile besides having sufficient molecular weight to be kept in the cured formulation. Higher molecular weight photoinitiator compounds usually have a lower migration potential, however generally sustain a loss of reactivity compared to lower molecular weight compounds.

The present invention describes macro-photoinitiators prepared by ring-opening addition of glycidoxylated benzophenones to di- and oligo amines. The products thus obtained are cheap and effective. Such macro-photoinitiators are in particular interesting for low migration/low emission applications.

Subject of the invention therefore is a photoinitiator compound comprising a photoactive moiety Q and an amine functionality, preferably a tertiary amino group, wherein Q is a photoactive moiety

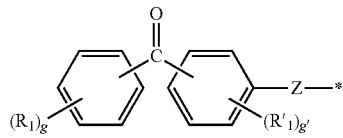

wherein the asterisk (*) denotes the bonding to the N atom;
g and g' independently of each other are an integer 0-5, in particular 0, 1 or 2;
$R_1$ and $R'_1$ independently of each other are hydrogen, linear or branched $C_1$-$C_6$alkyl, $OC_1$-$C_3$alkyl, $OR_3$, $NO_2$, CN, $(CO)OR_2$ or halogen;
Z is a group

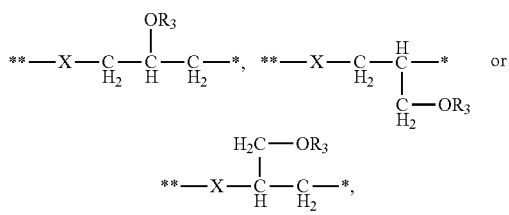

wherein the double asterisk (**) denotes the bonding to the phenyl ring and the asterisk (*) denotes the bonding to the nitrogen atom;
X is O, S or $OCH_2CH_2O$;
$R_2$ is hydrogen or linear or branched $C_1$-$C_6$alkyl; and
$R_3$ is hydrogen or $(CO)CH_3$.

The compounds of the invention are characterized by combining a photoinitiator and an amine moiety in one molecule and they exhibit a high cure speed, which could not be expected.

The compounds represent benzophenone-type macro-photoinitiators that are potentially suitable for low migration/low emission applications such as e.g. printing inks for food packaging.

The increased reactivity vs. benchmark is provided by the tertiary amino groups present in the backbone which act as co-initiator and which increase cure speed by virtue of reducing oxygen inhibition. This is a feature especially useful in thin film applications such as e.g. printing inks.

In the present invention the chemical bonding of the low molecular weight photoinitiators to the backbone is provided by 3-amino-2-hydroxy propyl ether groups instead. These groups are inherently stable with respect to both thermal and hydrolytic cleavage, thus excluding undesired release of low molecular weight photoinitiators.

In particular interesting are photoinitiator compounds as described above represented by formula (1)

wherein
$R_4$ and $R_5$ independently of each other are
a photoactive moiety Q;
hydrogen;
linear or branched $C_1$-$C_{20}$alkyl which optionally is substituted by one or more identical or different $Y_2$;
or $R_4$ and $R_5$ are linear or branched $C_2$-$C_{20}$alkyl which is interrupted by one or more identical or different $Y_1$ and which interrupted $C_2$-$C_{20}$alkyl optionally is substituted by one or more identical or different $Y_2$;
or $R_4$ and $R_5$ are $C_6$-$C_{14}$aryl which optionally is substituted by one or more identical or different $Y_3$;
or $R_4$ and $R_5$ are $C_6$-$C_{14}$aryl-$C_1$-$C_{20}$alkyl wherein the $C_6$-$C_{14}$aryl part optionally is substituted by one or more identical or different $Y_3$, and wherein the $C_1$-$C_{20}$alkyl part is unsubstituted or substituted by one or more identical or different $Y_2$;
or $R_4$ and $R_5$ are $C_6$-$C_{14}$aryl-$C_2$-$C_{20}$alkyl wherein the $C_2$-$C_{20}$alkyl part is interrupted by one or more identical or different $Y_1$, and wherein the $C_6$-$C_{14}$aryl part optionally is substituted by one or more identical or different $Y_3$, and wherein said interrupted $C_2$-$C_{20}$alkyl part is unsubstituted or substituted by one or more identical or different $Y_2$;
or $R_4$ and $R_5$ are $C_6$-$C_{14}$aryl-Y-$C_1$-$C_{20}$alkyl wherein the $C_1$-$C_{20}$alkyl part optionally is substituted by one or more identical or different $Y_2$, and wherein the $C_6$-$C_{14}$aryl part is unsubstituted or substituted by one or more identical or different $Y_3$;
or $R_4$ and $R_5$ are $C_6$-$C_{14}$aryl-Y-$C_2$-$C_{20}$alkyl wherein the $C_2$-$C_{20}$alkyl part is interrupted by one or more identical or different $Y_1$, and wherein the $C_6$-$C_{14}$aryl part optionally is substituted by one or more identical or different $Y_3$, and wherein said interrupted $C_2$-$C_{20}$alkyl part is unsubstituted or substituted by one or more identical or different $Y_2$;
or $R_4$ and $R_5$ are $C_5$-$C_{12}$cycloalkyl which optionally is substituted by one or more identical or different $Y_2$ or and/or by $C_1$-$C_3$alkyl;
or $R_4$ and $R_5$ together with the N atom to which they are bonded form a group

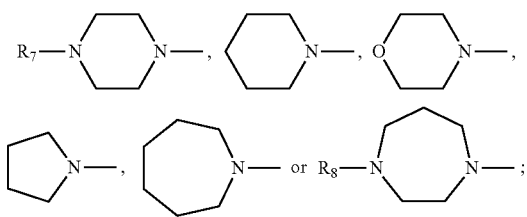

or $R_4$ and $R_5$ independenly of each other are a group $E-R_9$;

$R_6$ has one of the meanings as given for $R_4$ and $R_5$ or is $N(R_{10})(R_{11})$, $OR_{12}$, a group $E_1-R_{13}$, a group $E_2-R_{14}$, a group $E_3-R_{15}$ or

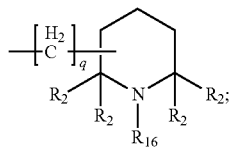

q is 0 or 1;

Q is a photoactive moiety

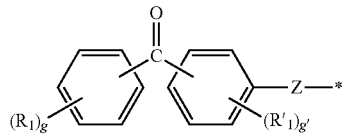

wherein the asterisk (*) denotes the bonding to the N atom;

g and g' independently of each other are an integer 0-5, in particular 0, 1 or 2;

$R_1$ and $R'_1$ independently of each other are hydrogen, linear or branched $C_1$-$C_6$alkyl, $OC_1$-$C_3$alkyl, $OR_3$, $NO_2$, CN, (CO)$OR_2$ or halogen;

Z is a group

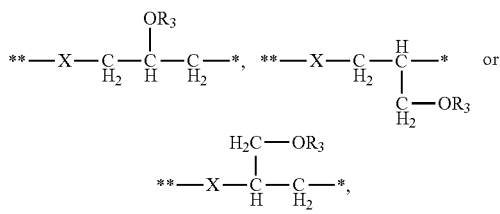

wherein the double asterisk (**) denotes the bonding to the phenyl ring and the asterisk (*) denotes the bonding to the nitrogen atom;

X is O, S or $OCH_2CH_2O$;

$R_2$ is hydrogen or $C_1$-$C_6$alkyl;

$R_3$ is hydrogen or (CO)$CH_3$;

Y is O, S or $N(R_{16})$;

$Y_1$ is $N(R_{16})$, O, S, S—S, $C(R_{17})$=$C(R_{18})$, phenylene, $C_5$-$C_6$cycloalkylene,

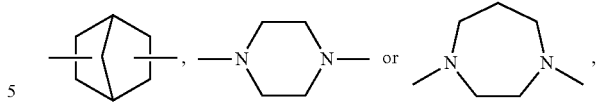

where several $Y_1$ in the same molcule are identical or different;

$Y_2$ is $N(R_{10})(R_{11})$, $OR_{12}$, SQ, $C(R_{17})$=$(R_{18})_2$, $CO(OR_2)$, $C_6$-$C_{14}$aryl or Y—$C_6$-$C_{14}$aryl which $C_6$-$C_{14}$aryl or Y—$C_6$-$C_{14}$aryl optionally is substituted by $Y_3$, where several $Y_2$ in the same molcule are identical or different;

$Y_3$ is halogen, CN, $NO_2$, OQ, SQ, $OR_{12}$, $N(R_{10})(R_{11})$, (CO)$OR_2$, $SO_3H$; phenyl or Ophenyl wherein said phenyl or Ophenyl optionally is substituted by one or more halogen, by linear or branched $C_1$-$C_3$alkyl or by linear or branched halo-$C_1$-$C_3$alkyl;

or $Y_3$ is linear or branched $C_1$-$C_6$alkyl which optionally is substituted by one or more halogen;

or $Y_3$ is linear or branched $C_1$-$C_3$alkyl which optionally is substituted by CN, SQ, $OR_{12}$, $N(R_{10})(R_{11})$ or (CO)$OR_2$, where several $Y_3$ in the same molcule are identical or different; $R_7$ and $R_8$ independently of each other are a photoactive moiety Q, hydrogen, linear or branched $C_1$-$C_6$alkyl which optionally is substituted by $OR_{12}$, CN, $C(R_{17})$=$C(R_{18})_2$, $C_6$-$C_{14}$aryl or by $OC_6$-$C_{14}$aryl wherein said $C_6$-$C_{14}$aryl or $OC_6$-$C_{14}$aryl optionally is substituted by $OR_{12}$, (CO)$OR_2$, halogen, CN, $NO_2$, linear or branched $C_1$-$C_6$alkyl or by linear or branched halo-$C_1$-$C_6$alkyl;

or $R_7$ and $R_8$ are linear or branched $C_2$-$C_{18}$alkyl which is interrupted by one or more O, (CO)O, O(CO), $C(R_{17})$=C$(R_{18})$ and which interrupted $C_2$-$C_{18}$alkyl optionally is substituted by $OR_{12}$, $C(R_{17})$=$C(R_{18})_2$ or by $NR_{10}R_{11}$;

or $R_7$ and $R_8$ are $C_5$-$C_6$cycloalkyl which optionally is substituted by $OR_{12}$;

or $R_7$ and $R_8$ are $C_6$-$C_{14}$aryl which optionally is substituted by $OR_{12}$, (CO)$OR_2$, halogen, CN, $NO_2$, linear or branched $C_1$-$C_6$alkyl or by linear or branched halo-$C_1$-$C_6$alkyl; $R_9$ is hydrogen, $G_2$-$N(R_{10})(R_{11})$, linear or branched $C_1$-$C_{20}$alkyl, linear or branched $C_2$-$C_6$alkenyl, phenyl, phenyl-$C_1$-$C_{20}$alkyl or (CO)$CH_3$;

$R_{10}$ and $R_{11}$ independently of each other are a photoactive moiety Q, hydrogen, linear or branched $C_1$-$C_6$alkyl which optionally is substituted by $OR_{12}$, CN, $C(R_{17})$=$C(R_{18})_2$, (CO)$OR_2$, $C_6$-$C_{14}$aryl or by $OC_6$-$C_{14}$aryl wherein said $C_6$-$C_{14}$aryl or $OC_6$-$C_{14}$aryl optionally is substituted by $OR_{12}$, (CO)$OR_2$, halogen, CN, $NO_2$, linear or branched $C_1$-$C_6$alkyl or linear or branched halo-$C_1$-$C_6$alkyl;

or $R_{10}$ and $R_{11}$ are linear or branched $C_2$-$C_{18}$alkyl which is interrupted by one or more O, (CO)O, O(CO), $C(R_{17})$=C$(R_{17})$ and which interrupted $C_2$-$C_{18}$alkyl optionally is substituted by $OR_{12}$, $C(R_{17})$=$C(R_{17})_2$ or by $N(C_1$-$C_6$alkyl)$_2$;

or $R_{10}$ and $R_{11}$ are $C_5$-$C_6$cycloalkyl which optionally is substituted by $OR_{12}$;

or $R_{10}$ and $R_{11}$ are $C_6$-$C_{14}$aryl which optionally is substituted by $OR_{12}$, (CO)$OR_2$, halogen, CN, $NO_2$, linear or branched $C_1$-$C_6$alkyl or by linear or branched halo-$C_1$-$C_6$alkyl;

or $R_{10}$ and $R_{11}$ together with the N atom to which they are bonded form a group $R'_7$ and $R'_8$ independently of each other have one of the meanings as given for $R_7$ and $R_8$;

$R_{12}$ has one of the definitions given for $R_2$ or is $(CO)CH_3$;

$R_{13}$ is hydrogen, $N(R_{10})(R_{11})$, OH, $O(CO)CH_3$ or $OC_2$-$C_6$alkenyl;

$R_{14}$ is $N(R_{10})(R_{11})$;

$R_{15}$ is hydrogen or $N(R_{10})(R_{11})$;

$R_{10}$ has one of the meanings as given for $R_7$ and $R_8$ or is a group -G- $N(R_{19})(R_{20})$;

$R_{17}$ and $R_{18}$ independently of each other have one of the definitions given for $R_2$;

$R_{19}$ and $R_{20}$ independently of each other have one of the definitions as given for $R_{10}$ and $R_{11}$;

or $R_{19}$ and $R_{20}$ independently of each other are a group -$G_1$-$N(R_{21})(R_{22})$;

G and $G_1$ independently of each other are linear or branched $C_2$-$C_6$alkylene;

$R_{21}$ and $R_{22}$ independently of each other have one of the definitions as given for $R_{10}$ and $R_{11}$;

E is a group $$*\!-\!\!+\!G_2\!-\!M\!+\!\!\!-_a$$

wherein the asterix (*) denotes the bond to the N-atom;

$G_2$ in the multiple occuring moiety $$*\!-\!\!+\!G_2\!-\!M\!+\!\!\!-_a$$

are identical or different and are linear or branched $C_2$-$C_6$alkylene;

a in the multiple occurring moiety $$*\!-\!\!+\!G_2\!-\!M\!+\!\!\!-_a$$

independently are an integer 1-50;

$E_1$ is a group wherein the asterix (*) denotes the bond to the N-atom;

M in the multiple occurring moieties are identical or different and are O or $N(R_{16})$;

e is 0 or 1;

$G_3$ in the multiple occurring moieties are identical or different and are linear or branched $C_2$-$C_6$alkylene;

the sum of b+c+d is an integer 1-50;

$R_{23}$ is hydrogen or linear or branched $C_1$-$C_6$alkyl;

or $R_{23}$, if e is 1, additionally is a group and in this case the sum of f+b+c+d is an integer 1-50;

$G_4$ in the multiple moieties $$-\!\!+\!G_4\!-\!M\!+\!\!\!-_f$$

are identical or different and are linear or branched $C_2$-$C_6$alkylene;

$R_{24}$ has one of the definitions as given for $R_{13}$;

$E_2$ is a group $E_3$ is a divalent ring system comprising a five- or six-membered aromatic or aliphatic ring optionally annellated by phenylene, and which five- or six-membered non-anellated or annellated aromatic ring comprises one or more identical or different Y or which five- or six-membered non-anellated or annellated aliphatic ring comprises one or more identical or different Y' and which two-valent ring system is unsubstituted or substituted by one or more identical or different $Y_3$;

Y' has one of the definitions as given for Y or is (CO);

$R_{25}$ and $R'_{25}$ independently of each other are linear or branched $C_1$-$C_6$alkyl;

$R_{26}$ and $R_{27}$ independently of each other are hydrogen, linear or branched $C_1$-$C_6$alkyl which optionally is substituted by halogen, or $R_{26}$ and $R_{27}$ together with the C atom to which they are bonded form a group

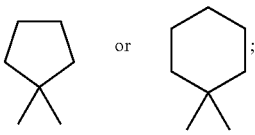

$G_5$ is cyclohexylene or phenylene, which cyclohexylene or phenylene optionally is substituted by linear or branched $C_1$-$C_6$alkyl;

$G_6$ is cyclohexylene or phenylene, which cyclohexylene or phenylene optionally is substituted by linear or branched $C_1$-$C_6$alkyl or $N(R_{10})(R_{11})$;

$G_7$ has one of the definitions as given for $G_5$;

$G_8$ is a direct bond or -Ophenylene, wherein the double asterisk () denotes the bond to the aromatic ring;

$G_9$ is a direct bond, $C(R_{26})(R_{27})$, O, S, $SO_2$, $N(R_{16})$ or

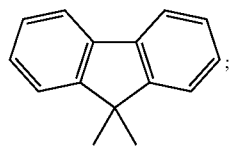

and $R_{28}$ and $R'_{28}$ are linear or branched $C_1$-$C_6$alkyl, halogen, $NO_2$ or $(CO)OR_2$;

provided that the compound of formula (1) comprises at least one group Q and that at least one of the defined amine moieties in the molecule is a tertiary amine.

$C_1$-$C_{20}$alkyl is linear or branched and is, for example, $C_1$-$C_{18}$-, $C_1$-$C_{14}$-, $C_1$-$C_{12}$-, $C_1$-$C_8$-, $C_1$-$C_6$-, $C_1$-$C_4$alkyl or $C_1$-$C_3$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl. $C_1$-$C_6$alkyl and $C_1$-$C_3$alkyl have the same meanings as given above for $C_1$-$C_{20}$alkyl up to the corresponding number of C-atoms.

$C_2$-$C_{20}$alkyl interrupted by one or more identical or different radicals (e.g. $Y_1$ as defined above) is for example interrupted 1-25, 1-20, 1-18, 1-12, 1-10, 1-9, 1-7 or once or twice. The interrupted $C_2$-$C_{20}$alkyl, is linear or branched and is for example interrupted $C_2$-$C_{12}$-, $C_2$-$C_{10}$-, $C_2$-$C_8$-, $C_4$-$C_{20}$-, $C_4$-$C_{12}$- or $C_2$-$C_{18}$alkyl. In case the groups are interrupted by more than one radicals or groups, e.g. $Y_1$, said radicals or groups, e.g $Y_1$, are separated from one another by at least one methylene group, i.e. the $Y_1$ are non-consecutive. Examples are the following structural units —$CH_2$—$Y_1$—$CH_3$, —$CH_2CH_2$—$Y_1$—$CH_2CH_3$, —[$CH_2CH_2Y_1$]—$CH_3$, with y=1-9, —($CH_2CH_2Yr_1$)$_7$$CH_2CH_3$, —$CH_2$—$CH(CH_3)$—$Y_1$—$CH_2$—$CH_2CH_3$, or —$CH_2$—$CH(CH_3)$—$Y_1$—$CH_2CH_3$ (these examples in particular apply if $Y_1$ is O).

Interrupted $C_2$-$C_{18}$alkyl has the same meanings as given above up to the corresponding number of C-atoms.

Halo-$C_1$-$C_6$alkyl and halo-$C_1$-$C_3$alkyl is linear or branched $C_1$-$C_6$alkyl or $C_1$-$C_3$alkyl as defined above which is substituted by one or more halogen. The halogen may replace all hydrogen atoms of the alkyl group, however preferably only one halogen is present, where halogen is as defined below.

$C_5$-$C_{12}$cycloalkyl is for example cyclopentyl, cyclohexyl, cyclooctyl, cyclo-dodecyl, especially cyclopentyl and cyclohexyl, preferably cyclohexyl.

Alkyl, interrupted alkyl and cycloalkyl which are substituted by one or more identical or different $Y_2$ are for example substituted 1-4 times, 1-3 or once or twice by $Y_2$.

Phenyl-$C_1$-$C_{20}$alkyl refers to linear or branched $C_1$-$C_{20}$alkyl as described above which is substituted by phenyl. Examples are benzyl, phenylethyl, α-methylbenzyl, phenylpentyl, phenylhexyl, phenyldodecyl etc. or α,α-dimethylbenzyl, especially benzyl.

$C_6$-$C_{14}$aryl is for example phenyl, naphthyl, anthryl or phenanthryl, in particular phenyl or naphthyl, preferably phenyl.

Substituted $C_6$-$C_{14}$aryl is for example substituted one to five times, e.g. once, twice or three times, in particular once or twice.

$C_6$-$C_{14}$aryl-$C_1$-$C_{20}$alkyl refers to linear or branched $C_1$-$C_{20}$alkyl, as decribed above, substituted with $C_6$-$C_{14}$aryl as described above.

$C_6$-$C_{14}$aryl-$C_2$-$C_{20}$alkyl, wherein the $C_2$-$C_{20}$alkyl part is interrupted by one or more identical or different radicals (e.g. $Y_1$ as defined above), refers to interrupted $C_2$-$C_{20}$alkyl as defined above, which is substituted with $C_6$-$C_{14}$aryl as defined above.

In the definitions $C_6$-$C_{14}$aryl-Y-$C_1$-$C_{20}$alkyl and $C_6$-$C_{14}$aryl-Y-$C_2$-$C_{20}$alkyl, wherein the $C_2$-$C_{20}$alkyl part is interrupted by one or more identical or different radicals (e.g. $Y_1$), $C_6$-$C_{14}$aryl, $C_1$-$C_{20}$alkyl and interrupted $C_2$-$C_{20}$alkyl are as defined above.

Halogen refers to Br, Cl, F and I, especially to Br and Cl and in particular to Cl when the halogen is directly positioned at an aromatic ring; while F is preferred as substituent at an alkyl group also an alkyl group as a side chain of on aromatic ring.

$C_2$-$C_4$alkenyl is mono or polyunsaturated, linear or branched and is for example $C_2$-$C_4$alkenyl. Examples are allyl, methallyl, vinyl, 1,1-dimethylallyl, 1-butenyl, 3-butenyl, 2-butenyl, 1,3-pentadienyl or 5-hexenyl, especially allyl or vinyl.

$C_2$-$C_6$alkylene is linear or branched alkylene, for example methylene, ethylene, propylene, 1-methylethylene 1,1-dimethylethylene, butylene, 1-methylpropylene, 2-methylpropylene, pentylene or hexylene.

$C_5$-$C_6$ycloalkylene is cyclopentylene or cyclohexylene.

Non-exhaustive examples of divalent ring systems as defined for $E_3$ are

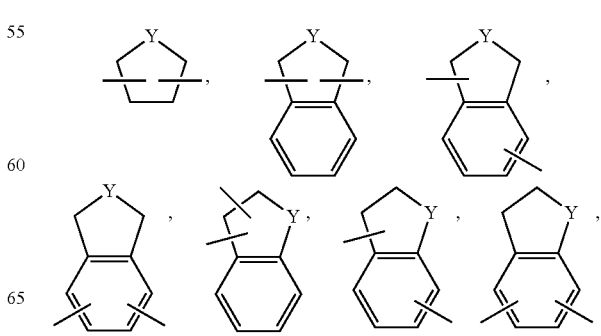

-continued

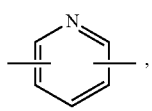

etc., in particular where Y denotes O, S or N(R$_{10}$), as defined above.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated in this text for the compounds according to the present invention in the context of this invention are intended to refer to all categories of the claims, that is to the mixtures, compositions, use, process, coated substrate claims as well.

The photoinitiator compound of formula (1) comprises at least one group Q. The photoinitiator compound of formula (1) for example comprises at least one group Q and at least one amine functionality, preferably a tert. amine functionality.

The photoinitiator compound of the present invention for example has a molecular weight of up to 5'000 g/mol, preferably of up to 2-500 g/mol, or for example 500-5'000 g/mol, 750-5'000 g/mol, preferably 500-2'500 g/mol or 750-2'500 g/mol.

a independently of each other are an integer 1-50; for example 2-50, 1-30, 10-50, 1-40, 1-10. a in different groups

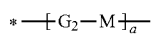

in the molecule are identical or different

The sum of b+c+d is an integer 1-50; for example 2-50, 1-30, 10-50, 1-40, 1-10.

g and g' in particular are 0, 1 or 2, for example are 0 or 1, especially are 0.

R$_1$ and R'$_1$ for example are independently of each other are hydrogen, linear or branched C$_1$-C$_6$alkyl or halogen; in particular are hydrogen or linear or branched C$_1$-C$_1$alkyl, especially are hydrogen.

Z is for example a group

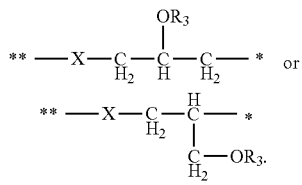

Or Z is for example a group

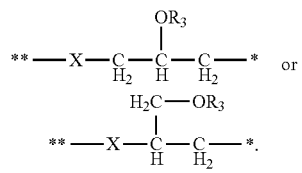

Z in particular is a group

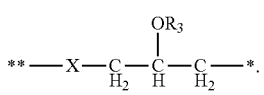

X is for example O or S. or X is for example O or OCH$_2$CH$_2$O. X preferably is O.

R$_4$ and R$_5$ for example independently of each other are a photoactive moiety Q; linear or branched C$_1$-C$_{20}$alkyl which optionally is substituted by one or more identical or different Y$_2$;

or $R_4$ and $R_5$ are linear or branched $C_2$-$C_{20}$alkyl which is interrupted by one or more identical or different $Y_1$ and which interrupted $C_2$-$C_{20}$alkyl optionally is substituted by one or more identical or different $Y_2$;

or $R_4$ and $R_5$ are $C_6$-$C_{14}$aryl-$C_2$-$C_{20}$alkyl wherein the $C_2$-$C_{20}$alkyl part is interrupted by one or more identical or different $Y_1$, and wherein the $C_6$-$C_{14}$aryl part optionally is substituted by one or more identical or different $Y_3$, and wherein said interrupted $C_2$-$C_{20}$alkyl part is unsubstituted or substituted by one or more identical or different $Y_2$;

or $R_4$ and $R_5$ are $C_5$-$C_{12}$cycloalkyl which optionally is substituted by one or more identical or different $Y_2$ or and/or by linear or branched $C_1$-$C_3$alkyl;

or $R_4$ and $R_5$ together with the N atom to which they are bonded form a group

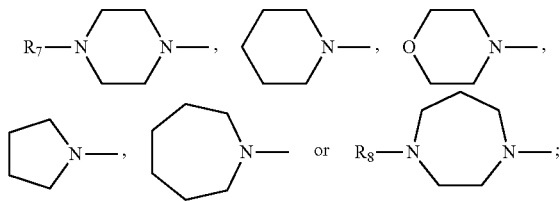

or $R_4$ and $R_5$ independenly of each other a group E-$R_9$.

For example $R_4$ and $R_5$ independently of each other are a photoactive moiety Q;

linear or branched $C_1$-$C_{20}$alkyl which optionally is substituted by one or more identical or different $Y_2$; or are a group E-$R_9$.

In particular $R_4$ and $R_5$ independently of each other are a photoactive moiety Q.

$R_6$ for example has one of the meanings as given for $R_4$ and $R_5$ as defined above, or is a group $E_1$-$R_{13}$, a group $E_2$-$R_{14}$, a group $E_3$-$R_{15}$ or

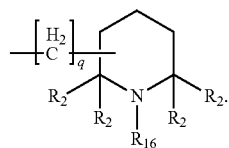

$R_6$ is for example linear or branched $C_1$-$C_{20}$alkyl which optionally is substituted by one or more identical or different $Y_2$; or $R_6$ is a group E-$R_9$ or a group $E_1$-$R_{13}$.

Y is for example O or S; or is for example O or N($R_{16}$); or is for example S or N($R_{16}$); preferably Y is O.

$Y_1$ is for example N($R_{16}$), O, S or S—S; or is for example N($R_{16}$), O or S; or is for example N($R_{16}$) or O; N($R_{16}$) or S; or is O or S.

$Y_2$ for example is N($R_{10}$)($R_{11}$), O$R_{12}$, SQ, C($R_{17}$)=($R_{18}$)$_2$ or (CO)O$R_2$; or $Y_2$ is for example N($R_{10}$)($R_{11}$), O$R_{12}$, SQ or (CO)O$R_2$; or is for example N($R_{10}$)($R_{11}$) or O$R_{12}$, in particular N($R_{10}$)($R_{11}$).

$Y_3$ is for example halogen, CN, NO$_2$, OQ, SQ, O$R_{12}$, N($R_{10}$)($R_{11}$), (CO)O$R_2$, SO$_3$H; phenyl or Ophenyl; or $Y_3$ is linear or branched $C_1$-$C_6$alkyl which optionally is substituted by one or more halogen; or $Y_3$ is linear or branched $C_1$-$C_3$alkyl which optionally is substituted by CN, SQ, O$R_{12}$, N($R_{10}$)($R_{11}$) or (CO)O$R_2$;

or $Y_3$ for example is SQ, O$R_{12}$, N($R_{10}$)($R_{11}$), (CO)O$R_2$, phenyl or Ophenyl or linear or branched $C_1$-$C_6$alkyl which optionally is substituted by one or more halogen; or for example is O$R_{12}$ or N($R_{10}$)($R_{11}$).

$R_7$ and $R_8$ independently of each other are for example a photoactive moiety Q, hydrogen, linear or branched $C_1$-$C_6$alkyl which optionally is substituted by O$R_{12}$, CN, C($R_{17}$)=C($R_{18}$)$_2$, $C_6$-$C_{14}$aryl or by $C_6$-$C_{14}$aryl wherein said $C_6$-$C_{14}$aryl or C-$C_{14}$aryl optionally is substituted by O$R_{12}$, (CO)O$R_2$, halogen, CN, NO2, $C_1$-$C_6$alkyl or by linear or branched halo-$C_1$-$C_6$alkyl;

or $R_7$ and $R_8$ are linear or branched $C_2$-$C_{18}$alkyl which is interrupted by O, (CO)O, O(CO), C($R_{17}$)=C($R_{18}$) and which interrupted $C_2$-$C_{18}$alkyl optionally is substituted by O$R_{12}$, C($R_{17}$)=C($R_{18}$)$_2$ or by N($C_1$-$C_6$alkyl)$_2$;

or $R_7$ and $R_8$ for example are a photoactive moiety Q or linear or branched $C_2$-$C_{18}$alkyl which is interrupted by O and which interrupted $C_2$-$C_{18}$alkyl optionally is substituted by O$R_{12}$.

$R'_7$ and $R'_8$ independently of each other have one of the meanings as given for $R_7$ and $R_8$ above.

$R_9$ is for example hydrogen, N($R_{10}$)($R_{11}$), $G_2$-N($R_{10}$)($R_{11}$), linear or branched $C_1$-$C_{20}$alkyl, linear or branched $C_2$-$C_6$alkenyl, phenyl, phenyl-$C_1$-$C_{20}$alkyl or (CO)CH$_3$; or is for example hydrogen, N($R_{10}$)($R_{11}$), or linear or branched $C_1$-$C_{20}$alkyl; or is for example N($R_{10}$)($R_{11}$), $G_2$-N($R_{10}$)($R_{11}$), linear or branched $C_1$-$C_{20}$alkyl, in particular N($R_{10}$)($R_{11}$).

$R_{10}$ and $R_{11}$ independently of each other are for example a photoactive moiety Q, hydrogen, linear or branched $C_1$-$C_6$alkyl which optionally is substituted by O$R_{12}$;

or $R_{10}$ and $R_{11}$ are linear or branched $C_2$-$C_{18}$alkyl which is interrupted by O, (CO)O, O(CO), and which interrupted $C_2$-$C_{18}$alkyl optionally is substituted by O$R_{12}$ or by N($C_1$-$C_6$alkyl)$_2$;

or $R_{10}$ and $R_{11}$ are $C_5$-$C_6$cycloalkyl which optionally is substituted by O$R_{12}$;

or $R_{10}$ and $R_{11}$ together with the N atom to which they are bonded form a group

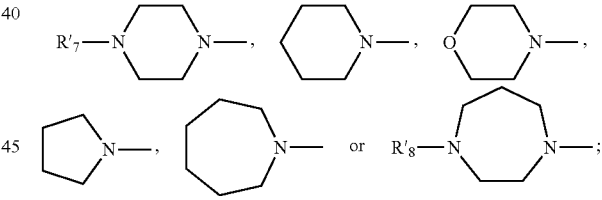

or $R_{10}$ and $R_{11}$ independently of each other are for example a photoactive moiety Q,;

or $R_{10}$ and $R_{11}$ are linear or branched $C_2$-$C_{18}$alkyl which is interrupted by O, and which interrupted $C_2$-$C_{18}$alkyl optionally is substituted by O$R_{12}$ or by N($C_1$-$C_6$alkyl)$_2$;

$R_{10}$ and $R_{11}$ in particular are $R_{10}$ and $R_{11}$ independently of each other are for example a photoactive moiety Q,;

or $R_{10}$ and $R_{11}$ are linear or branched $C_2$-$C_{18}$alkyl which is interrupted by O, and which interrupted $C_2$-$C_{18}$alkyl optionally is substituted by O$R_{12}$.

$R_{12}$ for example has one of the definitions given for $R_2$, in particular is hydrogen;

$R_{13}$ is for example hydrogen, N($R_{10}$)($R_{11}$) or OH; or is for example hydrogen, N($R_{10}$)($R_{11}$) or O(CO)CH$_3$; or is for example hydrogen N($R_{10}$)($R_{11}$) or or O$C_2$-$C_6$alkenyl; in particular is N($R_{10}$)($R_{11}$).

$R_{16}$ for example has one of the meanings as given for $R_7$ and $R_8$; $R_{16}$ for example is a photoactive moiety Q or is linear or branched $C_2$-$C_{18}$alkyl which is interrupted by O, and which interrupted $C_2$-$C_{10}$alkyl optionally is substituted by $OR_{12}$.

$R_{17}$ and $R_{18}$ independently of each other have one of the definitions given for $R_2$; including the preferences as given for $R_2$ above.

$R_{19}$ and $R_{20}$ independently of each other have one of the definitions as given for $R_{10}$ and $R_{11}$, including the preferences as given for $R_{10}$ and $R_{11}$ above, or $R_{19}$ and $R_{20}$ independently of each other are a group -$G_1$-$N(R_{21})(R_{22})$;

$R_{21}$ and $R_{22}$ independently of each other have one of the definitions as given for $R_{10}$ and $R_{11}$, including the preferences as given for $R_{10}$ and $R_{11}$ above.

E is a group $$*-[G_2-M]_a-,$$

wherein me asterix (*) denotes the bond to the N-atom.

$G_2$ in the multiple moieties $$*-[G_2-M]_a$$

are identical or different and are linear or branched $C_2$-$C_6$alkylene; in other words, the alkylene $G_2$ in said structural units does not mandatorily have always the same number of C-atoms in each unit. That is the group for example may be composed like $$*-[C_2\text{alkylene-M}]_A-[C_3\text{alkylene-M}]_B-$$

(with the sum of A+B=a) or $$-[C_3\text{alkylene-M}]_A-[C_2\text{alkylene-M}]_B-[C_3\text{alkylene-M}]_C-$$

(with the sum of A+B+C=a), etc.

M in the multiple occurring moieties $$*-[G_2-M]_a-, \quad -[G_3-M]_b-, \quad -[G_3-M]_c- \text{ or}$$
$$-[G_3-M]_d-$$

are identical or different and are O or $N(R_{16})$; in other words more than one M in one molecule can have both meanings O and $NR_{16}$ simultaneously for different parts of the defined molecule.

a in the multiple, optionally different moieties $$*-[G_2-M]_a-$$

independently for each moiety are an integer 1-50; for example an integer 1-25, 2-25, 1-15 or for example 2-15. In other words, the values a are not mandatorily identical for multiple groups $$*-[G_2-M]_a-.$$

e is 0 or 1, in particular 1.

$E_1$ is a group

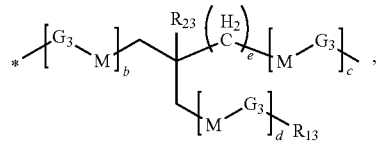

wherein the asterix (*) denotes the bond to the N-atom.

$G_3$ in the multiple moieties $$-[G_3-M]_b-, \quad -[G_3-M]_c- \text{ or } -[G_3-M]_d-$$

are identical or different and are linear or branched $C_2$-$C_6$alkylene; in other words, the alkylene $G_2$ in said structural units does not mandatorily have always the same number of C-atoms in each unit. That is the group for example may be composed like $$-[C_2\text{alkylene-M}]_B-[C_3\text{alkylene-M}]_C-$$

(with the sum of B+C=b), etc . . . Further, in the same molecule, the multiple $G_3$ in $$-[G_3-M]_b-, \quad -[G_3-M]_c- \text{ or } -[G_3-M]_d-$$

must not mandatorily be identical.

The sum of b+c+d is an integer 1-50; ; for example an integer 1-25, 2-25, 1-15 or for example 2-15.

$R_{23}$ for example is hydrogen or linear or branched $C_1$-$C_6$alkyl, in particular linear or branched $C_1$-$C_6$alkyl, or $R_{23}$, if e is 1, additionally is a group $$-\underset{H_2}{C}-[O-G_4]_f-R_{24};$$

and in this case the sum of f+b+c+d is an integer 1-50. Prefereably $R_{23}$ is linear or branched $C_1$-$C_6$alkyl.

$G_4$ in the multiple moieties $$-[G_4-O]_f-$$

are identical or different and are linear or branched $C_2$-$C_6$alkylene; in other words, the alkylene $G_2$ in said structural units does not mandatorily have always the same number of C-atoms in each unit. Similar as described above for $G_2$ and $G_3$.

$R_{24}$ has one of the definitions as given for $R_{13}$, including the preferences for $R_{13}$ as given above.

$E_2$ is for example a group

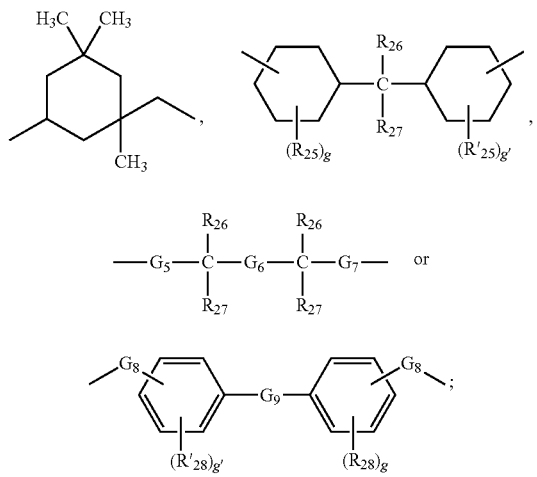

for example a group

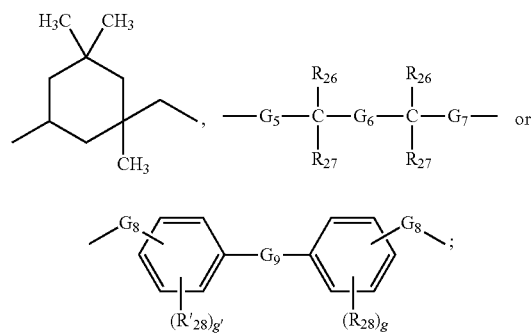

for example a group

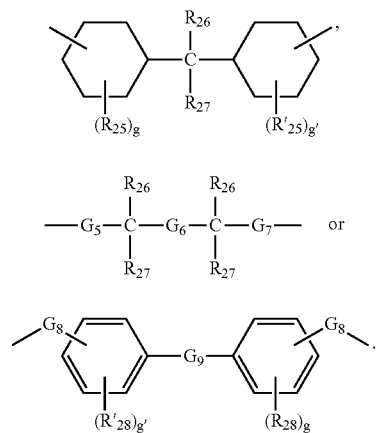

$E_3$ is for example a divalent ring system comprising a five- or six-membered aromatic or aliphatic ring optionally annellated by phenylene, and which five- or six-membered non-anellated or annellated aromatic ring comprises one or more identical or different Y or which five- or six-membered non-anellated or annellated aliphatic ring comprises one or more identical or different Y' and which two-valent ring system is unsubstituted or substituted by one or more identical or different $Y_3$; specific examples are as given above. $E_3$ for example is

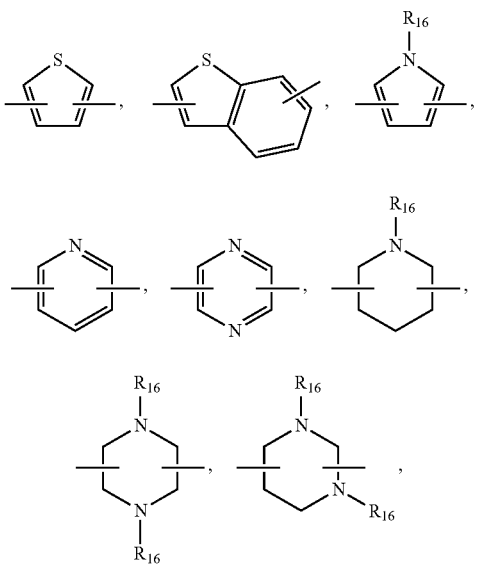

in particular

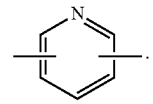

$R_{26}$ and $R_{27}$ for example are independently of each other are hydrogen, linear or branched $C_1$-$C_6$alkyl which optionally is substituted by halogen; or for example are hydrogen, linear or branched $C_1$-$C_6$alkyl; or $R_{26}$ and $R_{27}$ for example together with the C atom to which they are bonded form a group

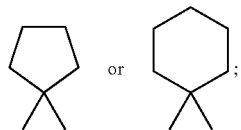

$R_{26}$ and $R_{27}$ especially are for example are hydrogen, linear or branched $C_1$-$C_6$alkyl.

$G_5$ is for example cyclohexylene or phenylene, which cyclohexylene or phenylene optionally is substituted by linear or branched $C_1$-$C_6$alkyl; in particular $G_5$ is unsubstituted cyclohexylene or phenylene.

$G_6$ is cyclohexylene or phenylene, which cyclohexylene or phenylene optionally is substituted by linear or branched $C_1$-$C_6$alkyl or $N(R_{10})(R_{11})$; in particular $G_6$ is unsubstituted cyclohexylene or phenylene.

$G_7$ has one of the definitions as given for $G_5$; including the preferences as given for $G_5$ above.

$G_8$ is for example a direct bond or -Ophenylene, wherein the double asterisk () denotes the bond to the aromatic ring; in particular is a direct bond.

$G_9$ is for example a direct bond, $C(R_{26})(R_{27})$, O, S, $SO_2$, $N(R_{16})$ or

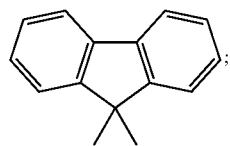

or is for example a direct bond, $C(R_{26})(R_{27})$, O, S or $N(R_{16})$, in particular a direct bond, $C(R_{26})(R_{27})$ or O; especially a direct bond or $C(R_{26})(R_{27})$.

$R_{28}$ and $R'_{28}$ are linear or branched $C_1$-$C_6$alkyl, halogen, $NO_2$ or $(CO)OR_2$; in particular are linear or branched $C_1$-$C_6$alkyl.

Preferred are photoinitiator compounds of the formula (1) as described above, wherein $R_4$ and $R_5$ are a photoactive moiety Q;

$R_6$ is linear or branched $C_1$-$C_{20}$alkyl which optionally is substituted by one or more identical or different $Y_2$;

or is linear or branched $C_2$-$C_{20}$alkyl which is interrupted by one or more identical or different $Y_1$ and which interrupted $C_2$-$C_{20}$alkyl optionally is substituted by one or more identical or different $Y_2$;

or is a group $E$-$R_9$ or $E_1$-$R_{13}$;

Q is a photoactive moiety

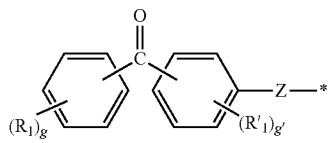

wherein the asterisk (*) denotes the bonding to the N atom;
g and g' are 0;
Z is a group

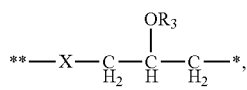

wherein the double asterisk (**) denotes the bonding to the phenyl ring and the asterisk (*)denotes the bonding to the nitrogen atom;

X is O;
$R_3$ is hydrogen or $(CO)CH_3$;
$Y_1$ is O or $NR_{16}$;
$Y_2$ is $N(R_{10})(R_{11})$;
$R_9$ is $G_2$-$N(R_{10})(R_{11})$ or hydrogen;
$R_{10}$ and $R_{11}$ independently of each other are a photoactive moiety Q, hydrogen,
or $R_{10}$ and $R_{11}$ are linear or branched $C_2$-$C_{18}$alkyl which is interrupted by one or more O and which interrupted $C_2$-$C_{18}$salkyl optionally is substituted by $OR_{12}$;
$R_{12}$ is hydrogen;
$R_{13}$ is $N(R_{10})(R_{11})$;
$R_{16}$ is a photoactive moiety Q, hydrogen, or linear or branched $C_2$-$C_{18}$alkyl which is interrupted by one or more O and which interrupted $C_2$-$C_{18}$alkyl optionally is substituted by $OR_{12}$ or $NR_{10}R_{11}$;

E is a group

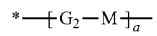

wherein me asterix (*) denotes the bond to the N-atom;
$G_2$ in the multiple occurring moieties

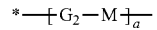

are identical or different and are linear or branched $C_2$-$C_6$alkylene;
a in the multiple occurring moieties

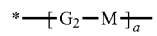

independently are an integer 1-50;
M in the multiple occuring moieties

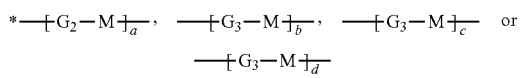

are identical or different and are O or $N(R_{16})$;
$E_1$ is a group

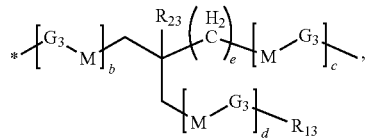

wherein the asterix (*) denotes the bond to the N-atom;
e is 1;
$G_3$ in the multiple occuring moieties $$-\!\!\!-\!\!\![G_3\!-\!M\,]_b\!-, \quad -\!\!\!-\!\!\![G_3\!-\!M\,]_c\!- \quad \text{or} \quad -\!\!\!-\!\!\![G_3\!-\!M\,]_d\!-$$

are identical or different and are linear or branched $C_2$-$C_6$alkylene; the sum of b+c+d is an integer 1-12; and $R_{23}$ is linear or branched $C_1$-$C_6$alkyl.

Subject of the invention also is a photoinitiator, comprising a mixture of one or more different compounds of the formula I; i.e. a photoinitiator mixture comprising more than one of the photoinitiator compounds as defined above.

The photoinitiator compounds of the present invention can be used singly or in any combination with each other. Subject of the invention therefore also is a photoinitiator comprising more than one, for example 2 or 3, in particular 2, of the photoinitiator compounds as described above.

The compounds of the present invention are for example prepared by a ring-opening addition of a (4-oxiranyl-methoxy-phenyl)-phenyl-methanone (which is optionally substituted at the phenyl rings) to di- and oligo amines according to the following schemes:

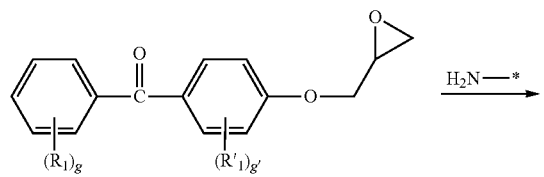

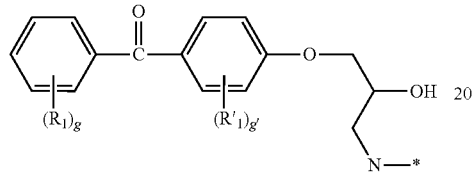

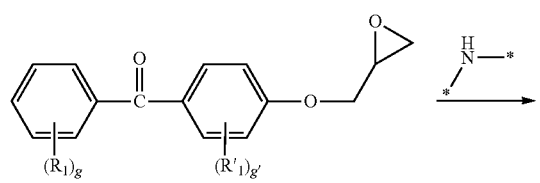

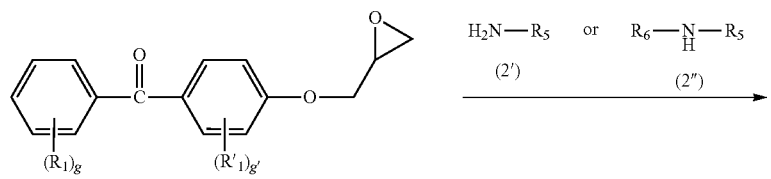

wherein $R_1$, $R'_1$, g and g' are defined as above and the asteriks' (*) denote the organic residue of the primary or tertiary amine.

Subject of the invention is a process for the preparation of compounds of the formula (1), $$\underset{R_5}{\overset{R_4}{N}}-R_6, \quad (1)$$

wherein $R_4$, $R_5$ and $R_6$ are as defined above, by ring-opening addition of a (4-oxiranylmethoxy-phenyl)-phenyl-methanone of the formula (10) to di- and oligo amines of formula (2') or (2")") to provide compounds of the formula (1') or (1") according to

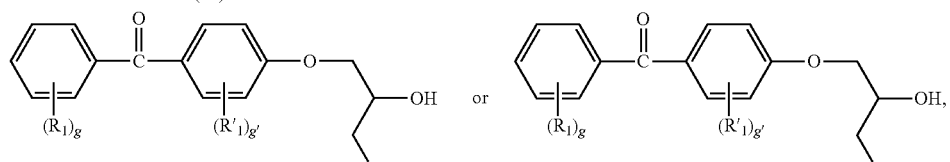

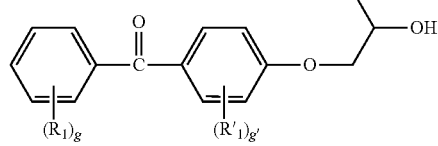

wherein $R_1$, $R'_1$, g, g', $R_5$ and $R_6$ are as defined above.

The starting material of the formula (10) is obtained by reacting the corresponding hydroxybenzophenone with epichlorohydrin.

Said reaction may provide structurally different reaction procucts, which, if used without separation will subsequently provide compounds with different structures after reaction with the amine, for example following the scheme:

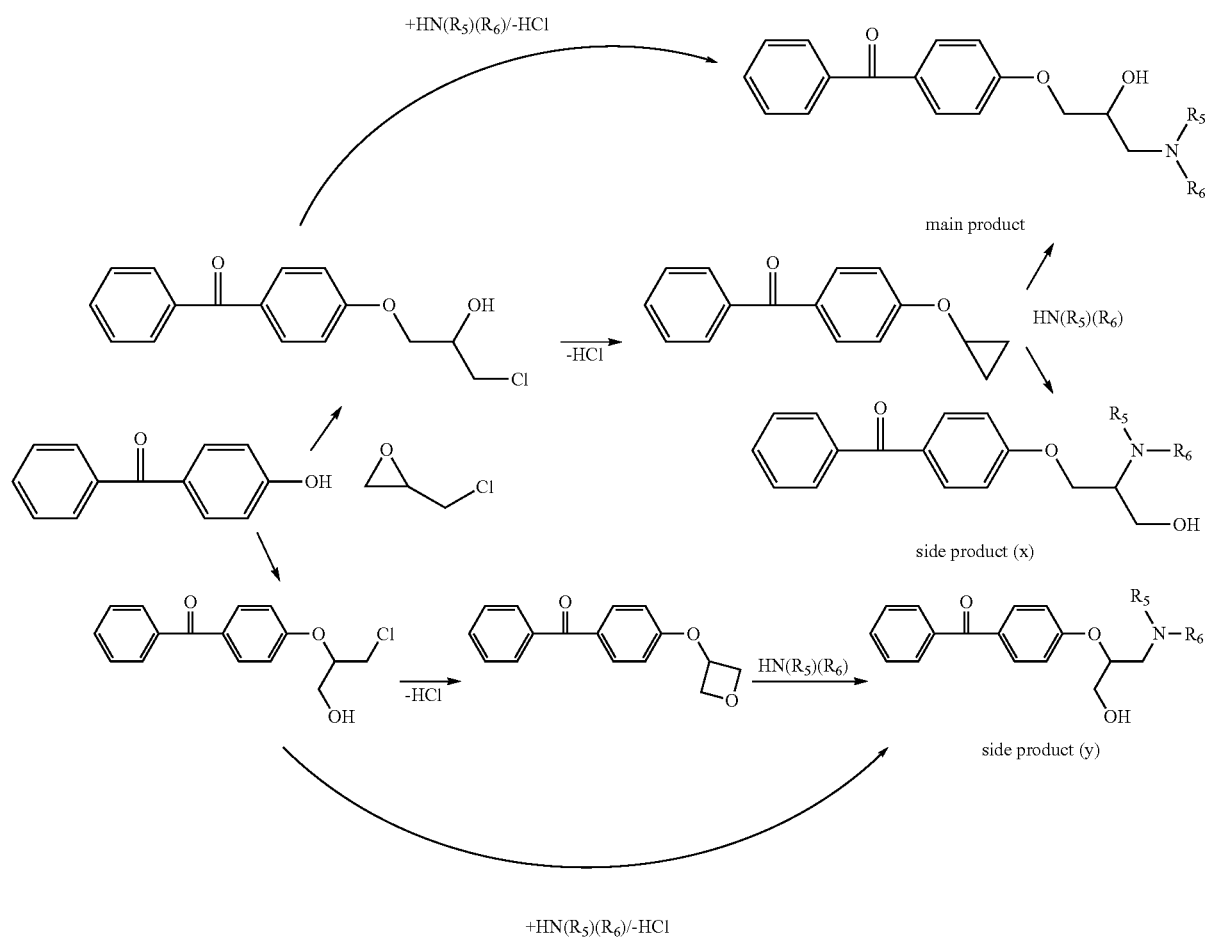
Examples of amines which are suitable as starting materials in the above reactions are:
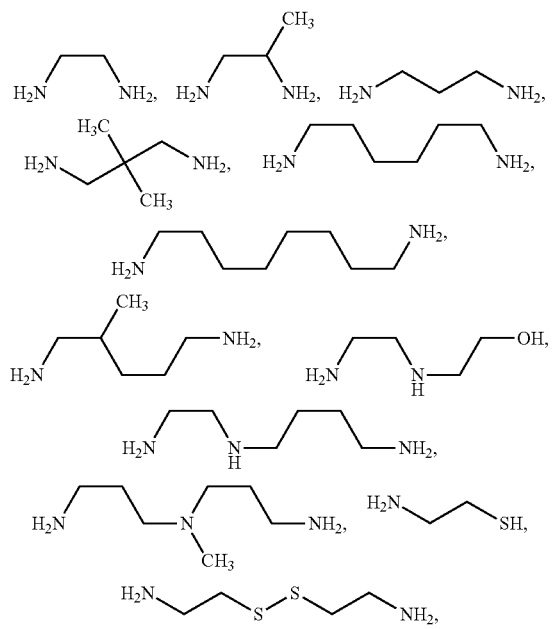
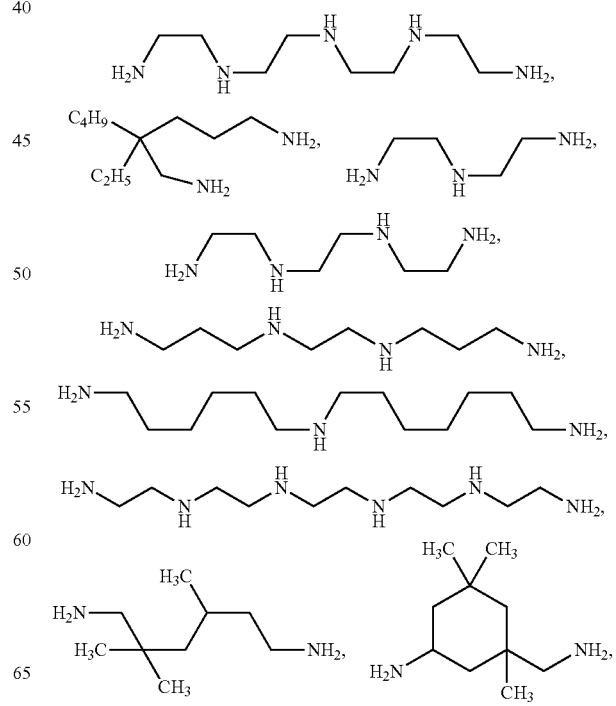

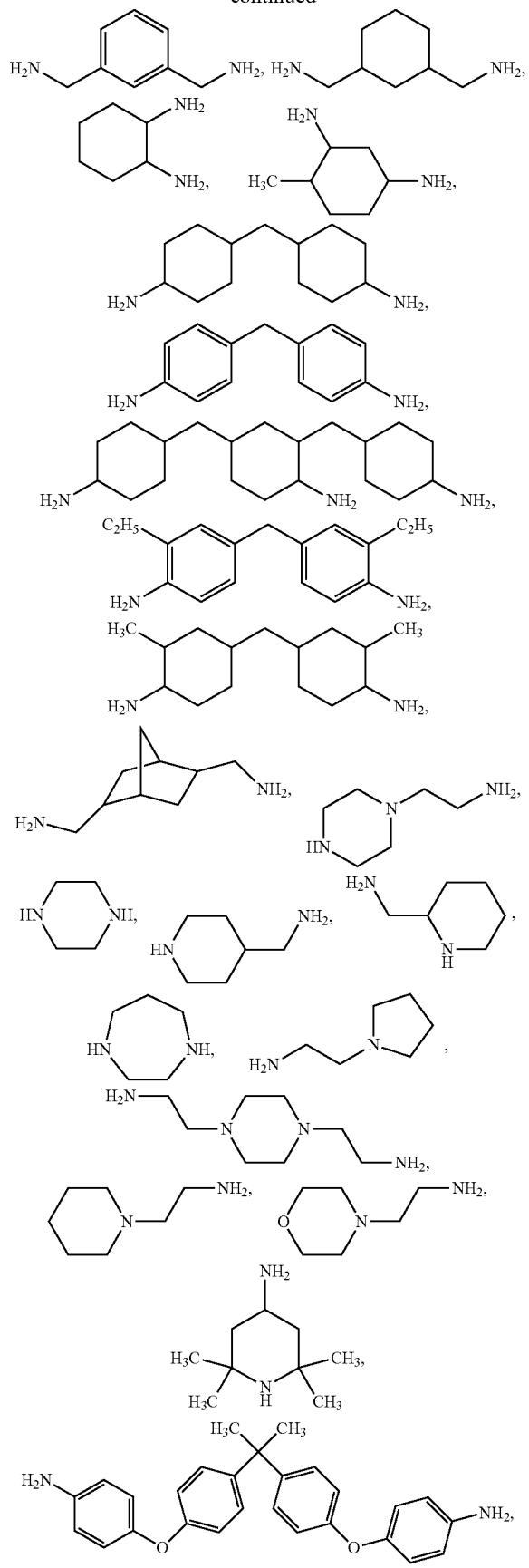
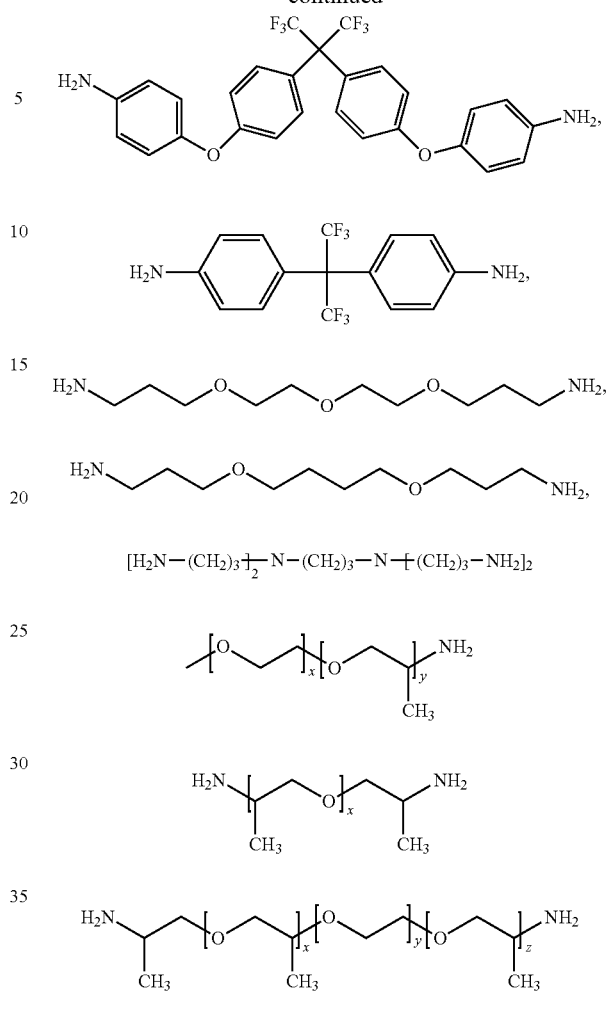

Polyethyleneimine (Lupasol GF, MW~800; Aldrich, MW~423)
Jeffamine M-600 (y/x = 9/1; MW ca. 600)
Jeffamine M-1000 (y/x = 3/19; MW ca. 1'000)
Jeffamine M-2005 (y/x = 29/6; MW ca. 2'000)
Jeffamine M-2070 (y/x = 10/31; MW ca. 2'000)
Jeffamine D-230 (x = 2.5; MW ca. 230)
Jeffamine D-400 (x =. 6.1; MW ca. 430)
Jeffamine D-2000 (x = 33; MW ca. 2'000)
Jeffamine HK-511 (y = 2, x + z = 1.2; MW ca. 220)
Jeffamine ED-600 (y = 9, x + z = 3.6; MW ca. 600)
Jeffamine ED-900 (y = 12.5, x + z = 6; MW ca. 900)
Jeffamine ED-2003 (y = 39, x + z = 6; MW ca. 2'000)
Jeffamine EDR-148 (x = 2; MW 148)
Jeffamine EDR-176 (x = 3; MW 176)
Jeffamine XTJ-435 (MW ca. 315)

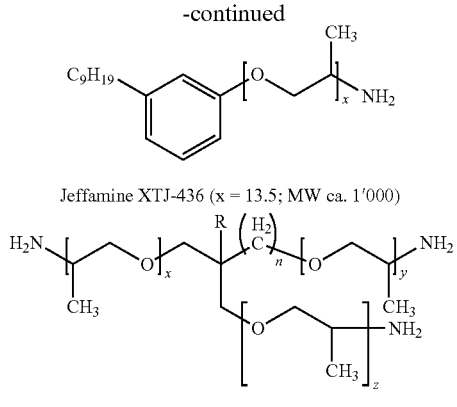

Jeffamine XTJ-436 (x = 13.5; MW ca. 1'000)

Jeffamine T-403 (R = C$_2$H$_5$, n = 1, x + y + z = 5-6; MW ca 440)
Jeffamine T-3000 (R = H, n = 0, x + y + z = 50; MW ca 3'000)

as well as

Jeffamine SD and ST series (from Jeffamine D and T series via —NH$_2$ ⇒ —NH(iso-propyl) transformation)

Jeffamine SD-231 (from D-230; MW ca. 315)
Jeffamine SD-401 (from D-400; MW ca. 515)
Jeffamine SD-2001 (from D-2000; MW ca. 2050)
Jeffamine ST-404 (from T-403; MW ca. 565)
Jeffamine XTJ-568 and XTJ-566 (analogues of Jeffamine D-230 and T-403 obtained by amination of butylene capped alcohols)
Jeffamine XTJ-582
Jeffamine XTJ-578

The above list is by no means intended to be exhaustive, in particular not intended to be limiting the scope of the invention.

Preferably, the amines in the reaction are completely conversed into tertiary amines in order to avoid side reactions, like for example a thermal crosslinking of remaining primary and secondary amines with the acrlyates in a Micheal addition reactions. Therefore, either Q is used in a small stoichiometric excess and the excess of Q for example optionally is removed after the reaction, or Q is employed in below the stoichiometric value and the alkylation is completed via an alkylation agent (epoxide, epoyether, etc.), and the excess of the alkylation agent after the reaction is removed (e.g. by distillation). Usually the reaction is carried out in a solvent, e.g. a protic solvent such as for example methanol, ethanol, i-propanol, n-propanol, 1-butanol, 2-butanol or mixtures of protic solvents (e.g. the ones as mentioned hereinbefore) with aprotic solvents as for example acetone, methylisobutyl ketone (MIBK), tetrahydrofurane (THF), N-methyl-pyrrolidone (NMP), dimethylfomramide (DMF), chloroform, dichloromethane, acetonitril, toluene etc.

The reaction temperatures in principle depend on the boiling point of the solvent which is used and are for example 25° C. to boiling point of the solvent, e.g. prefereably 50° C.-125° C.

The reaction time depends on the wanted grade of alkylation, and the reaction temperatures. Usually the reaction times are in the range of some hours up to 24 h, e.g. at temperatures about 60° C.-70° C. The reaction times reduce with higher reaction temperatures, increased pressure and or, the use of catalyst.

Suitable catalysts are known to the person skilled in the art and described e.g. in Houben-Weyl, Methoden der organischen Chemie, Georg Thieme Verlag, Stuttgart, vol. VI/3, pp. 465 (1965), vol. XI/1, pp. 311 (1957) and particularly, vol. E$_{16}$d, pp. 1202 (1992).. Used are for example (non-exhaustive enumeration) Lewis-acids, Brønstedt acids, Brønstedt bases, transition metal complexes or metal organyls such as e.g. (non-exhaustive enumeration) ZnCl$_2$, tartaric acid zinc salts, AlCl$_3$, HCl, Zeolithes, Al$_2$O$_3$, Pd[P(phenyl)$_3$]$_4$, butyl lithium etc.

In accordance with the invention, the photoinitiator compounds comprising a photo-active moiety Q and an amine functionality (e.g. the compounds of the formula I) can be used as photoinitiators for the photopolymerization of ethylenically unsaturated compounds or of mixtures which comprise such compounds.

The invention therefore also relates to photopolymerizable compositions comprising (A) at least one ethylenically unsaturated photopolymerizable compound and (B) at least one photoinitiator as defined above or a photoinitiator mixture as defined above.

The composition may comprise additionally to the component (B) at least one further photoinitiator (C) and/or other customary additives (D).

The ethylenically unsaturated photopolymerizable compound is monomeric or oligomeric. The unsaturated compounds (A) for example contain one or more olefinic double bonds. They are of low molecular weight (monomeric) or higher molecular weight (oligomeric).

Examples of monomers containing a double bond are (meth)acrylic acid and salts thereof, (meth)acrylic acid esters, e.g. alkyl esters such as methyl, ethyl, 2-chloroethyl, N-dimethylaminoethyl, n-butyl, isobutyl, pentyl, hexyl, cyclohexyl, 2-ethylhexyl, octyl, isobornyl [2-exobornyl] ester, phenyl, benzyl and o-, m- and p-hydroxyphenyl ester, hydroxyalkyl esters, e.g. 2-hydroxyethyl, 2-hydroxypropyl, 4-hydroxybutyl, 3,4-dihydroxybutyl or glycerol [1,2,3-propanetriol] ester, epoxyalkyl esters, e.g. glycidyl, 2,3-epoxybutyl, 3,4-epoxybutyl, 2,3-epoxycyclohexyl, 10,11-epoxyundecyl ester, (meth)acrylamides, N-substituted (meth) acrylamides, e.g. N-methylolacrylamide, N-methylolmethacrylamide, N-ethylacrylamide, N-ethylmethacrylamide, N-hexylacrylamide, N-hexylmethacrylamide, N-cyclohexylacrylamide, N-cyclohexylmethacrylamide, N-hydroxyethylacrylamide, N-phenylacrylamide, N-phenyl-methacrylamide, N-benzylacrylamide, N-benzylmethacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide and N-(4-hydroxyphenyl)methacrylamide, IBMAA (N-isobutoxymethylacrylamide), (meth)acrylonitriles, unsaturated acid anhydrides such as itaconic anhydride, maleic anhydride, 2,3-dimethylmaleic anhydride, 2-chloromaleic anhydride, unsaturated esters such as maleic acid esters, phthalic acid esters, itaconic acid esters [methylenesuccinic acid esters], styrenes such as methylstyrene, chloromethylstyrene and o-, m- and p-hydroxystyrene, divinylbenzene, vinyl ethers such as isobutyl vinyl ether, ethyl vinyl ether, 2-chloroethyl vinyl ether, hydroxyethyl vinyl ether, propyl vinyl ether, butyl vinyl ether, isobutyl vinyl ether, octyl vinyl ether and phenyl vinyl ether, vinyl and allyl esters such as vinyl acetate, vinyl acrylate, vinyl chloroacetate, vinyl butyrate and vinyl benzoate, divinyl succinate, diallyl phthalate, triallyl phosphate, vinyl chloride and vinylidene chloride, isocyanurates such as triallyl isocyanurate and tris(2-acryloylethyl) isocyanurate, N-vinyl-heterocyclic compounds such as N-vinyl pyrrolidones or substituted N-vinylpyrrolidones, N-vinylcaprolactam or substituted N-vinylcaprolactams, N-vinylcarbazole, N-vinylpyridine.

Further examples of suitable esters are:

diacrylate esters such as 1,6-hexanediol diacrylate (HDDA), ethylene glycol diacrylate, propylene glycol diacrylate, dipropylene glycol diacrylate, tripropylene glycol diacrylate, neopentyl glycol diacrylate, hexamethylene glycol diacrylate and bisphenol A diacrylate, trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having molecular weights of from 200 to 1500, or mixtures thereof.

Frequently also used are acrylic acid esters of alkoxylated alcohols, e.g. glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Examples of higher-molecular-weight unsaturated compounds (oligomers, prepolymers) are esters of ethylenically unsaturated mono- or poly-functional carboxylic acids and polyols or polyepoxides, and polymers having ethylenically unsaturated groups in the chain or in side groups such as, for example, unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more of such polymers.

Examples of suitable mono- or poly-functional unsaturated carboxylic acids are acrylic acid, methacrylic acid, crotonic acid, cinnamic acid, maleic acid, fumaric acid, itaconic acid, unsaturated fatty acids such as linolenic acid or oleic acid. Acrylic and methacrylic acid are preferred.

However, saturated di- or poly-carboxylic acids in admixture with unsaturated carboxylic acids may also be used. Examples of suitable saturated di- or poly-carboxylic acids include, for example, tetrachlorophthalic acid, tetrabromophthalic acid, phthalic anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid etc.

As polyols, aromatic and especially aliphatic and cycloaliphatic polyols are suitable. Examples of aromatic polyols are hydroquinone, 4,4'-dihydroxydiphenyl, 2,2-di(4-hydroxyphenyl)propane, and also novolaks and resols. Examples of polyepoxides are those based on the mentioned polyols, especially aromatic polyols and epichlorohydrin.

Also suitable as polyols are polymers and copolymers that contain hydroxyl groups in the polymer chain or in side groups such as, for example, polyvinyl alcohol and co-polymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Examples of polyurethanes are those composed of saturated diisocyanates and unsaturated diols or unsaturated diisocyanates and saturated diols.

Preference is given to methacrylated epoxy esters, methacrylated polyesters, polyesters carrying vinyl groups, methacrylated polyurethanes, methacrylated polyethers and polyols.

Suitable components (A) are also acrylates which have been modified by reaction with primary or secondary amines, as described, for example, in U.S. Pat. No. 3,844,916, in EP280222, in U.S. Pat. Nos. 5,482,649 or in 5,734,002. Such amine-modified acrylates are also termed amine acrylates. Amine acrylates are obtainable, for example, under the name EBECRYL 80, EBECRYL 81, EBECRYL 83, EBECRYL 7100 from UCB Chemicals, under the name Laromer PO 83F, Laromer PO 84F, Laromer PO 94F from BASF, under the name PHOTOMER 4775 F, PHOTOMER 4967 F from Cognis or under the name CN501, CN503, CN550 from Cray Valley and GENOMER 5275 from Rahn.

Some acrylate binders expecially designed for low extractables and odour applications can also be used in the formulation. Such resins are commercially available for example under the tradename Ebecryl LEO resins.

Furthermore, cationically UV-curable compositions may be used as part of component (A) for hybrid cationic/radical UV-curing. Such systems typically comprise aliphatic and/or aromatic epoxides, at least one polyol or polyvinyl polyol or oxetane and also at least one photoinitiator that generates cations. The said epoxides, polyols and polyvinyl polyols are known in the art and commercially available. The customarily used photoinitiators are iodonium and sulfonium salts as described, for example, in U.S. Pat. No. 6,306,555. In addition, ethylenically unsaturated compounds may be added to the said cationically UV-curable compositionsIt is also possible to add solvents or water to the compositions used in the process according to the invention. Suitable solvents are solvents which are known to the person skilled in the art and are conventional especially in surface-coating technology. Examples are various organic solvents such as, for example, ketones, e.g. methyl ethyl ketone, cyclohexanone; aromatic hydrocarbons, e.g. toluene, xylene or tetramethylbenzene; glycol ethers, e.g. diethylene glycol monoethyl ether, dipropylene glycol diethyl ether; esters, e.g. ethyl acetate; aliphatic hydrocarbons, e.g. hexane, octane, decane; or petroleum solvents, e.g. petroleum ether.

The invention relates also to compositions comprising, as component (A), at least one ethylenically unsaturated photopolymerisable compound dissolved or emulsified in water.

Such radiation-curable aqueous prepolymer dispersions are obtainable commercially in many variations. They are to be understood as being a dispersion consisting of water and at least one prepolymer dispersed therein. The concentration of the water in those systems is, for example, from 5 to 80% by weight, especially from 30 to 60% by weight. The radiation-curable prepolymer or prepolymer mixture is present in concentrations of, for example, from 95 to 20% by weight, especially from 70 to 40% by weight. The sum of the indicated percentages for water and prepolymer in those compositions is in each case 100; auxiliaries and additives, which are present in varying amounts depending on the intended use, are in addition thereto.

The radiation-curable film-forming prepolymers, which are dispersed or in many cases dissolved in water, are mono- or poly-functional ethylenically unsaturated prepolymers capable of initiation by free radicals and known per se for aqueous prepolymer dispersions; for example, they have a content of from 0.01 to 1.0 mol of polymerisable double bonds per 100 g of prepolymer and an average molecular weight of, for example, at least 400, especially from 500 to 10 000, although depending on the intended use prepolymers having higher molecular weights also come into consideration.

Used are, for example, polyesters containing polymerisable C—C double bonds and having an acid number of at most 10, polyethers containing polymerisable C—C double bonds, hydroxyl-group-containing reaction products of a polyepoxide containing at least two epoxide groups per molecule with at least one a,13-ethylenically unsaturated carboxylic acid, polyurethane (meth)acrylates and also acrylic copolymers containing $\alpha,\beta$-ethylenically unsaturated acrylic radicals as described, for example, in EP012339. Mixtures of those prepolymers may also be used. Also suitable are, for example, the polymerisable prepolymers described in EP033896, which are thioether adducts of polymerisable prepolymers having an average molecular weight of at least 600, a carboxyl group content of from 0.2 to 15% and a content of from 0.01 to 0.8 mol of polymerisable C—C double bonds per 100 g of prepolymer. Other suitable aqueous dispersions based on particular (meth)acrylic acid alkyl ester polymerisation products are described in EP041125; suitable water-dispersible, radiation-curable prepolymers obtained from urethane acrylates are to be found in, for example, $DE_{2936039}$.

The photopolymerisable compounds (A) are used singly or in any desired mixture.

Component (A) may also comprise binders, that being especially advantageous when the photopolymerisable compounds are liquid or viscous substances. The amount of the binder may be, for example, from 5 to 95% by weight, preferably from 10 to 90% by weight and especially from 40 to 90% by weight, based on the total solid material. The binder is selected according to the field of use and the properties required therefor such as, for example, developability in aqueous and organic solvent systems, adhesion to substrates and sensitivity to oxygen.

Suitable binders are, for example, polymers having molecular weights of about 5 000 -2 000 000, preferably 10 000-1 000 000. Examples are: homo- and co-polymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, e.g. cellulose acetate, cellulose acetate butyrate, methylcellulose, ethylcellulose; polyvinyl butyral, polyvinyl formal, cyclised rubber, polyethers, e.g. polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers, e.g. polycaprolactam and poly(hexamethylene adipamide), polyesters, e.g. poly(ethylene glycol terephthalate) and poly(hexamethylene glycol succinate).

The unsaturated compounds may also be used in admixture with non-photopolymerisable film-forming components. The latter are, for example, physically drying polymers or solutions thereof in organic solvents, e.g. nitrocellulose or cellulose acetobutyrate, but may also be chemically or thermally curable resins, e.g. polyisocyanates, polyepoxides or melamine resins. Melamine resins are to be understood as including not only condensation products of melamine (=1, 3,5-triazine-2,4,6-triamine) but also those of melamine derivatives. In general, the binder is a film-forming binder based on a thermoplastic or thermocurable resin, mainly a thermocurable resin. Examples thereof are alkyd, acrylic, polyester, phenol, melamine, epoxy and polyurethane resins and mixtures thereof. The concomitant use of thermally curable resins is of importance for use in so-called hybrid systems, which are both photopolymerised and also thermally crosslinked.

Component (A) may also comprise film-forming binders based on a thermoplastic or thermocurable resin, mainly a thermocurable resin. Examples thereof are alkyd, acrylic, polyester, phenol, melamine, epoxy and polyurethane resins and mixtures thereof. Examples thereof are described in, for example, Ullmann's Encyclopedia of Industrial Chemistry, 5th Ed., Vol. A18, pp. 368-426, VCH, Weinheim 1991.

The binder may be a binder that fully cures at cold or hot temperatures, for which the addition of a curing catalyst may be advantageous. Suitable catalysts which accelerate full curing of the binder are described in, for example, Ullmann's Encyclopedia of Industrial Chemistry, Vol. A18, p. 469, VCH Verlagsgesellschaft, Weinheim 1991.

WO99/03930; WO2000/010974 and WO2000/020517 describe maleimide-modified binders. Maleimide-modified binders of that kind may likewise be present in the photocurable composition of the present invention.

Examples of binders are:

1. surface-coatings based on cold- or hot-crosslinkable alkyd, acrylate, polyester, epoxy or melamine resins or mixtures of such resins, optionally with the addition of a curing catalyst;

2. two-component polyurethane surface-coating compositions based on hydroxyl-group-containing acrylate, polyester or polyether resins and aliphatic or aromatic isocyanates, isocyanurates or polyisocyanates;

3. two-component polyurethane surface-coating compositions based on thiol-group-containing acrylate, polyester or polyether resins and aliphatic or aromatic isocyanates, isocyanurates or polyisocyanates;

4. single-component polyurethane surface-coating compositions based on blocked isocyanates, isocyanurates or polyisocyanates, which are unblocked during stoving; optionally, the addition of melamine resins is also possible;

5. single-component polyurethane surface-coating compositions based on aliphatic or aromatic urethanes or polyurethanes and hydroxyl-group-containing acrylate, polyester or polyether resins;

6. single-component polyurethane surface-coating compositions based on aliphatic or aromatic urethane acrylates or polyurethane acrylates having free amine groups in the urethane structure, and melamine resins or polyether resins, optionally with the addition of a curing catalyst;

7. two-component surface-coating compositions based on (poly)ketimines and aliphatic or aromatic isocyanates, isocyanurates or polyisocyanates;

8. two-component surface-coating compositions based on (poly)ketimines and an unsaturated acrylate resin or a polyacetoacetate resin or a methacrylamidoglycolate methyl ester;

9. two-component surface-coating compositions based on carboxyl- or amino-group-containing polyacrylates and polyepoxides;

10. two-component surface-coating compositions based on anhydride-group-containing acrylate resins and a polyhydroxy or polyamino component;

11. two-component surface-coating compositions based on acrylate-containing anhydrides and polyepoxides;

12. two-component surface-coating compositions based on (poly)oxazolines and anhydride-group-containing acrylate resins or unsaturated acrylate resins or aliphatic or aromatic isocyanates, isocyanurates or polyisocyanates;

13. two-component surface-coating compositions based on unsaturated (poly)acrylates and (poly)malonates;

14. thermoplastic polyacrylate surface-coating compositions based on thermoplastic acrylate resins or extrinsically crosslinking acrylate resins, in combination with etherified melamine resins;

15. surface-coating systems, especially clearcoats, based on malonate-blocked isocyanates with melamine resins (e.g. hexamethoxymethyl melamine) as crosslinkers (acid-catalysed);

16. UV-curable systems based on oligomeric urethane acrylates and/or acylate acrylates, optionally with the addition of other oligomers or monomers;

17. dual-cure systems, which are first cured thermally and then UV-cured, or vice versa, wherein constituents of the surface-coating composition contain double bonds which can be made to react by UV light and photoinitiators and/or by electron-beam curing.

Both 1-component (1C) and 2-component (2C) systems may be used as binder. Examples of such systems are described in Ullmann's Encyclopedia of Industrial Chemistry, Vol. A18, Paints and Coatings, page 404-407, VCH Verlagsgesellschaft mbH, Weinheim (1991).

The composition can be optimised by specifically modifying the formulation, e.g. by varying the binder/crosslinker ratio. The person skilled in the art of coating or ink technology will be familiar with such measures.

The photopolymerizable composition of the invention for example additionally comprises a binder polymer (e), in particular a copolymer of methacrylate and methacrylic acid.

In addition to the photoinitiator, the photopolymerisable mixtures may comprise various additives (D). Examples thereof are thermal inhibitors, which are intended to prevent premature polymerisation, e.g. 2,2,6,6-tetramethyl-4-hydroxy-piperidin-1-oxyl (4-hydroxy-TEMPO) and derivatives thereof, e.g. bis(2,2,6,6-tetramethylpiperidin-1-oxyl-4-yl)-decanedioate or polyalkyl-piperidin-N-oxyl radicals, 3-arylbenzofuran-2-one and derivatives thereof, e.g. 5,7-di-tert-butyl-3-phenyl-3H-benzofuran-2-one (as described in, for example, WO01/42313), hydroquinone, hydroquinone derivatives, p-methoxyphenol, β-naphthol or sterically hindered phenols, e.g. 2,6-di(tert-butyl)-p-cresol. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethyl-ammonium chloride or trimethylbenzylammonium chloride, or hydroxylamine derivatives, e.g. N-diethylhydroxylamine. For the purpose of excluding atmospheric oxygen during polymerisation it is possible to add paraffin or similar wax-like substances which, being insoluble in the polymer, migrate to the surface at the beginning of the polymerisation and form a transparent surface layer which prevents air from entering. Equally possible is the application of a layer that is impermeable to oxygen.

As light stabilisers it is possible to add UV absorbers, e.g. those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS). Such compounds are widely known to the person skilled in the art.

Examples of such UV absorbers and light stabilisers are disclosed in WO04/074328, page 12, line 9 to page 14, line 23, said disclosure hereby is incorporated by reference. Further, additives that are customary in the art such as, for example, antistatics, flow improvers and adhesion promoters may be used.

In accordance with the invention, if the formulation comprises binder, thermal drying or curing catalysts may additionally be added to the formulation as additional additives (D). Possible drying catalysts, or thermal curing catalysts, are, for example, organic metal compounds, amines or/and phosphines. Organic metal compounds are, for example, metal carboxylates, especially those of the metals Pb, Mn, Hf, Co, Zn, Zr or Cu, or metal chelates, especially those of the metals Hf, Al, Ti or Zr, or organometal compounds, such as e.g. organotin compounds. Examples of metal carboxylates are the stearates of Pb, Mn or Zn, the octoates of Co, Zn or Cu, the naphthenates of Mn and Co or the corresponding linoleates or tallates (tall oil, which contains rosin acids, oleic and linoleic acids). Examples of metal chelates are the aluminium, titanium or zirconium chelates of acetyl acetone, ethylacetyl acetate, salicylaldehyde, salicylaldoxime, o-hydroxyacetophenone or ethyl-trifluoroacetyl acetate and the alkoxides of those metals. Examples of organotin compounds are dibutyltin oxide, dibutyltin dilaurate and dibutyltin dioctoate. Examples of amines are especially tertiary amines such as, for example, tributylamine, triethanolamine, N-methyldiethanolamine, N-dimethylethanolamine, N-ethylmorpholine, N-methylmorpholine and diazabicyclooctane (triethylenediamine) and the salts thereof. Further examples are quaternary ammonium salts, such as e.g. trimethylbenzylammonium chloride. It is also possible to use phosphines such as, for example, triphenylphosphine, as curing catalysts. Suitable catalysts are also described in, for example, J. Bielemann, Lackadditive, Wiley-VCH Verlag GmbH, Weinheim, 1998, pages 244-247. Examples are carboxylic acids such as, for example, p-toluenesulfonic acid, dodecylbenzenesulfonic acid, dinonylnaphthalenesulfonic acid and dinonylnaphthalenedisulfonic acid. There may also be used, for example, latent or blocked sulfonic acids, it being possible for the blocking of the acid to be ionic or non-ionic.

Such catalysts are used in concentrations customary in the art and known to the skilled person.

In order to accelerate photopolymerisation, amines may be added as further additives (D), especially tertiary amines, e.g. tributylamine, triethanolamine, p-dimethylaminobenzoic acid ethyl ester, Michler's ketone, N-methyl-diethanolamine, N-dimethylethanolamine, N-ethylmorpholine, N-methylmorpholine, diazabicyclooctane (triethylenediamine), 18-diazabicyclo[5.4.0]undec-7-ene (DBU), 1,5-diazabicyclo[4.3.0]non-5-ene (DBN) and salts thereof. Further examples are quaternary ammonium salts, e.g. trimethylbenzylammonium chloride. The action of the amines may be reinforced by adding aromatic ketones of the benzophenone type. Amines that are suitable as oxygen capture agents are, for example, N,N-dialkylanilines as described in EP339841. Further accelerators, coinitiators and auto-oxidisers are thiols, thioethers, disulfides and phosphines as described in, for example, EP438123 and GB2180358.

It is also possible for chain transfer reagents customary in the art to be added to the compositions according to the invention. Examples are mercaptans, amines and benzothiazole.

Photopolymerisation can also be accelerated by addition, as further additives (D), of photosensitisers, which shift or broaden the spectral sensitivity. These include especially aromatic carbonyl compounds such as, for example, benzophenone derivatives, thioxanthone derivatives, including especially isopropyl thioxanthone, anthraquinone derivatives and 3-acylcoumarin derivatives, terphenyls, styryl ketones, and 3-(aroylmethylene)-thiazolines, camphorquinone and also eosin, rhodamine and erythrosine dyes.

The amines mentioned above, for example, may also be regarded as photosensitisers. Examples of suitable sensitizer compounds (D) are disclosed in WO06/008251, page 36, line 30 to page 38, line 8, the disclosure of which is hereby incorporated by reference.

The curing process, especially of pigmented (e.g. pigmented with titanium dioxide) compositions, can also be assisted by adding an additional additive (D) which under thermal conditions is a free-radical-forming component, for example an azo compound, e.g. 2,2'-azobis(4-methoxy-2,4-dimethylvaleronitrile), a triazene, a diazo sulfide, a pentazadiene or a peroxy compound such as a hydroperoxide or peroxycarbonate, e.g. tert-butyl hydroperoxide as described in, for example, EP245639.

Further customary additives (D) are—depending on the intended use—fluorescent whitening agents, fillers, e.g. kaolin, talc, barite, gypsum, chalk or silicate-type fillers, wetting agents or flow improvers.

For curing thick and pigmented coatings, the addition of glass microspheres or powdered glass fibres is suitable, as described in, for example, U.S. Pat. No. 5,013,768.

The formulations may also comprise dyes and/or white or coloured pigments [as further additve (D)]. Depending on the intended use, both inorganic and organic pigments may be used. Such additives will be known to the person skilled in the art; a few examples are titanium dioxide pigments, e.g. of the rutile or anatase type, carbon black, zinc oxide, e.g. zinc white, iron oxides, e.g. iron oxide yellow, iron oxide red, chromium yellow, chromium green, nickel titanium yellow, ultramarine blue, cobalt blue, bismuth vanadate, cadmium yellow or cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketo-pyrrolo-pyrrole, isoindolinone, e.g. tetrachloroisoindolinone, isoindoline, dioxazine, benzimidazolone and quinophthalone pigments.

The pigments may be used in the formulations singly or in admixture.

The pigments are added to the formulations, in accordance with the intended use, in amounts customary in the art, for example in an amount of from 1 to 60% by weight, or from 10 to 30% by weight, based on the total mass.

The formulations may also comprise, for example, organic dyes from a very wide variety of classes. Examples are azo dyes, methine dyes, anthraquinone dyes or metal complex dyes. Customary concentrations are, for example, from 0.1 to 20%, especially from 1 to 5%, based on the total mass.

Selection of the additives is based on the particular field of use of the photopolymerizable composition and the properties desired in that field.

Subject of the invention also is a photopolymerizable composition as described above as further additive (D) comprising a pigment or dye or a mixture of pigments or dyes.

The additives (D) described hereinbefore are customary in the art and are accordingly used in amounts customary in the art.

The photoinitiator compounds of the formula (1) or mixtures of said compounds can also be used in admixture with reactive diluents, such as for example acrylates of polyols. Such reactive diluents are for example available under the tradenames SR (provided by Sartomer) or Laromer (provided by BASF). Examples are SR306 (tripropylene glycol diacrylate), SR344 (poylethylene glycol [PEG400] diacrylate), SR9020 (glyceryl propoxy triacrylate), SR355 (bistrimethylol propane tetraacrylate), SR295 (pentaerythritol tetraacrylate), SR494 (pentaerythritol polyethylene glycol ether tetraacrylate), SR399 (d ipentaerythritol pentaacrylate), DPHA=dipentaerythritol hexaacrylate, SR341 (amineacrylate), LAROMER TMPTA (trimethylolpropane triacrylate), LAROMER BDDA (butanediol diacrylate), LAROMER HDDA (hexanediol diacrylate), LAROMER TPGDA (tripropyleneglycol triacrylate), LAROMER DPGDA (dipropylenenglycol diacrylate), LAROMER LR 8863 (ethoxylated TMP triacrylate).

The above list is by no means intended to be exhaustive, in particular not intended to be limiting the scope of the invention.

It is, of course, possible to use mixtures of the compound of the invention with known photoinitiators (C), for example mixtures with camphor quinone; benzophenone, benzophenone derivatives, such as 2,4,6-trimethylbenzophenone, 2-methylbenzophenone, 3-methylbenzophenone, 4-methylbenzophenone, 2-methoxycarbonylbenzophenone 4,4'-bis(chloromethyl)benzophenone, 4-chlorobenzophenone, 4-phenylbenzophenone, 3,3'-d imethyl-4-methoxy-benzophenone, [4-(4-methylphenylthio)phenyl]-phenylmethanone, methyl-2-benzoyl benzoate, 3-methyl-4'-phenylbenzophenone, 2,4,6-trimethyl-4'-phenylbenzophenone, 4,4'-bis(dimethylamino)benzophenone, 4,4'-bis(diethylamino) benzophenone; ketal compounds, as for example benzildimethylketal; acetophenone, acetophenone derivatives, for example α-hydroxycycloalkyl phenyl ketones or α-hydroxyalkyl phenyl ketones, such as for example 2-hydroxy-2-methyl-1-phenyl-propanone, 1-hydroxy-cyclohexyl-phenyl-ketone, 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one; 2-hydroxy-1-{4-[4-(2-hydroxy-2-methyl-propionyl)-benzyl]-phenyl}-2-methyl-propan-1-one; 2-hydroxy-1-{4-[4-(2-hydroxy-2-methyl-propionyl)-phenoxy]-phenyl}-2-methyl-propan-1-one; oligomeric α-hydroxy ketones; dialkoxyacetophenones, α-hydroxy- or α-aminoacetophenones, e.g. (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (4-(2-hydroxyethyl) aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. methyl α-oxo benzeneacetate, oxo-phenyl-acetic acid 2-(2-hydroxy-ethoxy)-ethyl ester, dimeric phenylglyoxalic esters, e.g. oxo-phenyl-acetic acid 1-methyl-242-(2-oxo-2-phenyl-acetoxy)-propoxyFethyl ester; oximeesters, e.g. 1,2-octanedione 1[4-(phenylthio)phenyl]-2-(O-benzoyloxime), ethanone 1-[9-ethyl-6-(2-methylben-zoyl)-9H-carbazol-3-yl]-1-(O-acetyloxime), 9H-thioxan-thene-2-carboxaldehyde 9-oxo-2-(O-acetyloxime), or for example a combination of oxime esters with α-amino ketones, e.g. a combination of (4-morpholinobenzoyI)-1-benzyl-1-dimethylaminopropane with [4-(2-methylphenyl-carboxy)phenyI]-bis[4-(O-acetyloximine)phenyl]amine; peresters, e,g. benzophenone tetracarboxylic peresters as described for example in EP126541, monoacyl phosphine oxides, e.g. (2,4,6-trimethylbenzoyl)diphenylphosphine oxide, ethyl (2,4,6-trimethylbenzoyl phenyl) phosphinic acid ester; bisacylphosphine oxides, e.g. bis(2,6-dimethoxy-ben-zoyl)-(2,4,4-trimethyl-pentyl)phosphine oxide, bis(2,4,6-tri-methylbenzoyl)-phenylphosphine oxide, bis(2,4,6-trimeth-ylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]tri-azine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, hexaarylbisimidazole/coinitiator systems, e.g. ortho-chlorohexaphenyl-bisimidazole combined with 2-mercaptobenzthiazole, ferrocenium compounds, or titanocenes, e.g. bis(cyclopenta-dienyl)-bis(2,6-difluoro-3-pyrryl-phenyl)titanium. Further, borate compounds can be used as coinitiators.

Many of said additional photoinitiators (C) are commercially available, for example under the tradenames DAROCUR® and IRGACURE® from Ciba Inc. (part of BASF SE).

The photopolymerizable composition as described above for example comprises 0.05 to 15% by weight, preferably 0.1 to 5% by weight, of the photoinitiator (B) or the photoinitiators (B)+(C), based on the composition.

The compositions according to the invention can be used for various purposes, for example in overprint coatings, as printing ink, e.g. screen printing ink, ink for offset- or flexo printing, inkjet ink, ink for sheet-fed printing, electrophotography ink, intaglio ink, as clearcoats, white coats or colour-pigmented coats, e.g. for wood or metal, as powder coatings, as paints, inter alia for paper, wood, metal or plastics, as daylight-curable paints for marking structures and roads, paints for buidings, constructions, vehicles etc., for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as etch resists or permanent resists, both liquid and dry films, as photostructurable dielectrics, and as solder masks for electronic circuits, as resists in the production of colour filters for any type of display screen or in the creation of structures during the manufacture of plasma displays and electroluminescent displays, in the production of optical switches, optical gratings (interference gratings), in the manufacture of three-dimensional articles by curing in the mass (UV curing in transparent moulds) or according to the stereolithography process, as described in, for example, U.S. Pat. No. 4,575,330, in the manufacture of composite materials (e.g. styrene polyesters which may include glass fibres and/or other fibres and other adjuvants) of gel coats and thick-layered compositions, in the coating or sealing of electronic components or as coatings for optical fibres. The compositions are also suitable for the production of optical lenses, e.g. contact lenses or Fresnel lenses, and also in the manufacture of medical apparatus, aids or implants. The compositions can also be used for the preparation of gels having thermotropic properties. Such gels are described in, for example, DE19700064 and EP678534.

Photocuring further is of great importance for printing applications, since the drying time of the ink is a critical factor for the production rate of graphic products, and should be in the order of fractions of seconds. UV-curable inks are particularly important for screen printing, offset inks, ink-jet inks, flexographic printing inks, intaglio inks, electrophotographic inks, sheetfed inks, overprint varnishes or primers.

As already mentioned above, the novel photoinitiators are highly suitable also for producing printing plates e.g. flexo printing plates or offset printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Printing inks are known to the person skilled in the art, are used widely in the art and are described in the literature.

They are, for example, pigmented printing inks and printing inks coloured with dyes.

A printing ink is, for example, a liquid or paste-form dispersion that comprises colorants (pigments or dyes), binders and also optionally solvents and/or optionally water and additives. In a liquid printing ink, the binder and, if applicable, the additives are generally dissolved in a solvent. Customary viscosities in the Brookfield viscometer are, for example, from 20 to 5000 mPa·s, for example from 20 to 1000 mPa·s, for liquid printing inks. For paste-form printing inks, the values range, for example, from 1 to 100 Pa·s, preferably from 5 to 50 Pa·s. The person skilled in the art will be familiar with the ingredients and compositions of printing inks.

Suitable pigments, like the printing ink formulations customary in the art, are generally known and widely described.

Printing inks comprise pigments advantageously in a concentration of, for example, from 0.01 to 40% by weight, preferably from 1 to 25% by weight, especially from 5 to 15% by weight, based on the total weight of the printing ink.

The printing inks can be used, for example, for intaglio printing, gravure printing, flexographic printing, screen printing, offset printing, lithography or continuous or dropwise ink-jet printing on material pretreated in accordance with the process of the invention using generally known formulations, for example in publishing, packaging or shipping, in logistics, in advertising, in security printing or in the field of office equipment.

Suitable printing inks are both solvent-based printing inks and water-based printing inks.

Of interest are, for example, printing inks based on aqueous acrylate. Such inks are to be understood as including polymers or copolymers that are obtained by polymerisation of at least one monomer containing a group

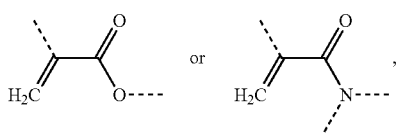

and that are dissolved in water or a water-containing organic solvent. Suitable organic solvents are water-miscible solvents customarily used by the person skilled in the art, for example alcohols, such as methanol, ethanol and isomers of propanol, butanol and pentanol, ethylene glycol and ethers thereof, such as ethylene glycol methyl ether and ethylene glycol ethyl ether, and ketones, such as acetone, ethyl methyl ketone or cyclo, for example isopropanol. Water and alcohols are preferred.

Suitable printing inks comprise, for example, as binder primarily an acrylate polymer or copolymer and the solvent is selected, for example, from the group consisting of water, $C_1$-$C_5$alcohols, ethylene glycol, 2-($C_1$-$C_5$alkoxy)-ethanol, acetone, ethyl methyl ketone and any mixtures thereof.

In addition to the binder, the printing inks may also comprise customary additives known to the person skilled in the art in customary concentrations.

For intaglio or flexographic printing, a printing ink is usually prepared by dilution of a printing ink concentrate and can then be used in accordance with methods known per se.

The printing inks may, for example, also comprise alkyd systems that dry oxidatively.

The printing inks are dried in a known manner customary in the art, optionally with heating of the coating.

A suitable aqueous printing ink composition comprises, for example, a pigment or a combination of pigments, a dispersant and a binder.

Subject of the invention therefore also is a photopolymerizable composition as described above as further additive (D) comprising a dispersant or a mixture of dispersants.

Dispersants that come into consideration include, for example, customary dispersants, such as water-soluble dispersants based on one or more arylsulfonic acid/formaldehyde condensation products or on one or more water-soluble oxalkylated phenols, non-ionic dispersants or polymeric acids. Such dispersants are known and are described, for example, in U.S. Pat. No. 5,186,846 and DE19727767. Suitable oxalkylated phenols are likewise known and are described, for example, in U.S. Pat. No. 4,218,218 and DE19727767. Suitable non-ionic dispersants are, for example, alkylene oxide adducts, polymerisation products of vinylpyrrolidone, vinyl acetate or vinyl alcohol and co- or terpolymers of vinyl pyrrolidone with vinyl acetate and/or vinyl alcohol.

It is also possible, for example, to use polymeric acids which act both as dispersants and as binders.

Examples of suitable binder components that may be mentioned include (meth-) acrylate-group-containing, vinyl-group-containing and/or, depending on the intended application, epoxy-group-containing monomers, prepolymers and polymers and mixtures thereof. Further examples are melamine acrylates and silicone acrylates. The acrylate compounds may also be non-ionically modified (e.g. provided with amino groups) or ionically modified (e.g. provided with acid groups or ammonium groups) and used in the form of aqueous dispersions or emulsions (e.g. EP704469, EP012339). Furthermore, in order to obtain the desired viscosity the solventless acrylate polymers can be mixed with so-called reactive diluents, for example vinyl-group-containing monomers. Further suitable binder components are epoxy-group-containing compounds.

The printing ink compositions may also comprise as additional components, for example, an agent having a water-retaining action (humectant), e.g. polyhydric alcohols, polyalkylene glycols, which renders the compositions especially suitable for ink-jet printing.

It will be understood that the printing inks may comprise further auxiliaries, such as are customary especially for (aqueous) ink-jet inks and in the printing and coating industries, for example preservatives (such as glutardialdehyde and/or tetramethylolacetyleneurea, anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. When such agents are present in the compositions, their total amount is generally ≤1% by weight, based on the weight of the preparation.

Printing inks include, for example, those comprising a dye (with a total content of dyes of e.g. from 1 to 35% by weight, based on the total weight of the ink). Dyes suitable for colouring such printing inks are known to the person skilled in the art and are widely available commercially, e.g. from Ciba AG, Basel.

Such printing inks may comprise organic solvents, e.g. water-miscible organic solvents, for example $C_1$-$C_4$alcohols, amides, ketones or ketone alcohols, ethers, nitrogen-containing heterocyclic compounds, polyalkylene glycols, $C_2$-$C_6$alkylene glycols and thioglycols, further polyols, e.g. glycerol and $C_1$-$C_4$alkyl ethers of polyhydric alcohols, usually in an amount of from 2 to 30% by weight, based on the total weight of the printing ink.

The printing inks may also, for example, comprise solubilisers, e.g. ε-caprolactam.

The printing inks may, inter alia for the purpose of adjusting the viscosity, comprise thickeners of natural or synthetic origin. Examples of thickeners include commercially available alginate thickeners, starch ethers or locust bean flour ethers. The printing inks comprise such thickeners e.g. in an amount of from 0.01 to 2% by weight, based on the total weight of the printing ink.

It is also possible for the printing inks to comprise buffer substances, for example borax, borate, phosphate, polyphosphate or citrate, in amounts of e.g. from 0.1 to 3% by weight, in order to establish a pH value of e.g. from 4 to 9, especially from 5 to 8.5.

As further additives, such printing inks may comprise surfactants or humectants. Surfactants that come into consideration include commercially available anionic and non-ionic surfactants. Humectants that come into consideration include, for example, urea or a mixture of sodium lactate (advantageously in the form of a 50 to 60% aqueous solution) and glycerol and/or propylene glycol in amounts of e.g. from 0.1 to 30% by weight, especially from 2 to 30% by weight, in the printing inks.

Furthermore, the printing inks may also comprise customary additives, for example foam-reducing agents or especially substances that inhibit the growth of fungi and/or bacteria. Such additives are usually used in amounts of from 0.01 to 1% by weight, based on the total weight of the printing ink.

The printing inks may also be prepared in customary manner by mixing the individual components together, for example in the desired amount of water.

As already mentioned, depending upon the nature of the use, it may be necessary for e.g. the viscosity or other physical properties of the printing ink, especially those properties which influence the affinity of the printing ink for the substrate in question, to be adapted accordingly.

The printing inks are also suitable, for example, for use in recording systems of the kind in which a printing ink is expressed from a small opening in the form of droplets which are directed towards a substrate on which an image is formed. Suitable substrates are, for example, textile fibre materials, paper, plastics or aluminium foils pretreated by the process according to the invention. Suitable recording systems are e.g. commercially available ink-jet printers.

Preference is given to printing processes in which aqueous printing inks are used.

Preferred in ink-jet ink formulations comprise (meth)acrylated epoxy esters; (meth)acrylated polyesters or vinyl-ether-group-containing polyesters, (meth)acrylated polyurethanes, polyethers and polyols.

A preferred component used in UV-curable inkjet are acrylates which have been modified by reaction with primary or secondary amines, as described, for example, in U.S. Pat. Nos. 3,844,916, EP280222, 5,482,649 or 5,734,002. Such amine-modified acrylates are also termed aminoacrylates. Examples are already given hereinbefore. It is known that in the presence of aminoacrylates UV-curable systems show an increased curing performance. They are useful to overcome the oxygen inhibition typically observed for radical induced polymerization reactions, especially for low viscous systems like UV-curable inkjet.

It will be clear that mixtures of all these cited monomers, prepolymers, polymers and oligomers can be used in the ink compositions comprising the novel photoinitiator according to the present invention.

The amount of the photopolymerizable monomer, oligomer or prepolymer in this connection is for example 10 to 80 wt %, preferably 10 to 60 wt %.

The inks comprising the photoinitiator of the present invention may besides to radically polymerizable components also comprise cationic-curable compositions having a low viscosity which comprise at least one aliphatic or aromatic epoxide, at least one polyol or polyvinyl polyols as mentioned above, and at least one cation-generating photoinitiator. A number of these epoxides are well known in the art and are commercially available. Photoinitiators that can be used in the cationic photocurable compositions are, for example, aryl iodonium salts and aryl sulfonium salts.

Emphasized are such hybrid systems that contain cationically and radically polymerisable and photopolymerisable raw materials. Examples of cationically polymerisable systems include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. Radiation curable resins contain ethylenically unsaturated compounds, especially (meth)acrylate resins. Examples are also as given above.

Furthermore interesting are hybrid systems that are photopolymerized in a first stage and then crosslinked through thermal post-treatment in a second stage or vice versa. Such hybrid systems comprise an unsaturated compound in admixture with non-photopolymerizable film-forming components. These may, for example, be physically drying polymers or solutions thereof in organic solvents, for example nitrocellulose or cellulose acetobutyrate. However, they may also be chemically or thermally curable resins, for example polyisocyanates, polyepoxides or melamine resins.

Other compositions suitable as for example ink-jet inks are dual cure compositions, which are cured first by heat and subsequently by UV or electron irradiation, or vice versa, and whose components contain ethylenic double bonds as described above capable to react on irradiation with UV light in presence of a photoinitiator, in the context of the invention the novel photoinitiator of formula (1) as described above.

Ink jet inks for example contain a colorant. A wide variety of organic and inorganic dyes and pigments, alone or in combination may be selected for use in ink jet ink compositions; the person skilled in the art is familiar with the appropriate coice. The pigment particles should be sufficiently small (0.005 to 15 µm) to permit free flow of the ink at the ejecting nozzles. The pigment particles should preferably be 0.005 to 1 µm.

Very fine dispersions of pigments and their preparation are disclosed in e.g. U.S. Pat. No. 5,538,548.

The inks preferably comprise a total content of colorant of 1 to 35% by weight, in particular 1 to 30% by weight, and preferably 1 to 20% by weight, based on the total weight of ink. A limit of 2.5% by weight, in particular 5% by weight, and preferably 7.5% by weight, is preferred here as the lower limit.

Suitable colorants are for example pure pigment powders such as Cyan IRGALITE® Blue GLO (Ciba Inc.) or pigment preparations such as MICROLITH-pigment preparations.

Ink jet inks may include a variety of further additives such as for example surfactants, biocides, buffering agents, anti-mold agents, pH adjustment agents, electric conductivity adjustment agents, chelating agents, anti-rusting agents, polymerisation inhibitors, light stabilizers, and the like. Such additives may be included in the ink jet inks in any effective amount, as desired.

A preferred field of use comprises overprint coatings and also pigmented thin coatings (layer thickness <20 µm), for example printing inks that are used in printing methods such as, for example, flexographic printing, offset printing, screen printing, intaglio printing, gravure printing, letterpress printing, tampon printing and inkjet printing.

Overprint coatings typically comprise ethylenically unsaturated compounds such as oligomeric and/or monomeric acrylates. Amine acrylates may also be included.

As mentioned hereinbefore, the overprint coatings and printing inks may also comprise further photoinitiators and coinitiators.

Subject of the invention therefore also is a photopolymerizable composition as described above, which is a printing ink, in particular an offset printing ink.

The photoinitiators of the present invention are also suitable for use in UV-curable adhesives; e.g. in the preparation of pressure-sensitive adhesives, laminating adhesives, hot-melt adhesives, moisture-cure adhesives, silane reactive adhesives or silane reactive sealants and the like, and related applications. Said adhesives can be hot melt adhesives as well waterborne or solvent borne adhesives, liquid solventless adhesives or 2-part reactive adhesives. In particular suitable are pressure-sensitive adhesives (PSA), for example uv-curable hot melt pressure sensitive adhesives. Said adhesives for example comprise at least one rubber component, at least one resin component as tackyfier and at least one oil component, for example in the weight ratio 30:50:20. Suitable able tackyfiers are natural or synthetic resins. The person skilled in the art is aware of suitable corresponding compounds as well as of suitable oil components or rubbers.

The pre-polymerized adhesives containing the isocyanates, for example in blocked form, can for example be processed at high temperature and coated onto the substrate following the hotmelt process, afterwards full cure is achieved by an additional curing step involving the blocked isocyanates, which is realized by photoactivation of the photolatent catalyst.

The compounds according to the invention may also be used as initiators for emulsion, bead or suspension polymerisation processes or as initiators of polymerisation for the fixing of orientation states of liquid-crystalline monomers and oligomers, or as initiators for the fixing of dyes on organic materials.

The compounds according to the invention and mixtures thereof may also be used as free-radical photoinitiators or photoinitiating systems for radiation-curable powder coatings. The powder coatings may be based on solid resins and monomers containing reactive double bonds, for example maleates, fumarates, vinyl ethers, (meth)acrylates, (meth) acrylamides and mixtures thereof. A free-radical UV-curable powder coating may be formulated by mixing unsaturated polyester resins with solid acrylamides (e.g. methylacrylamido-glycolate methyl ester) and a free-radical photoinitiator according to the invention, for example as described in the lecture "Radiation Curing of Powder Coating", Conference Proceedings, Radtech Europe 1993 by M. Wittig and Th. Gohmann. Free-radical UV-curable power coatings may also be formulated by mixing unsaturated polyester resins with solid acrylates, methacrylates or vinyl ethers and a photoinitiator (or photoinitiator mixture) according to the invention. The powder coatings may also comprise binders, as described in, for example, DE4228514 and EP636669. The powder coating formulations described in EP636669 comprise, for example, a) an unsaturated resin from the group of (semi-) crystalline or amorphous unsaturated polyesters, unsaturated polyacrylates or mixtures thereof with unsaturated polyesters, with special preference being given to those derived from maleic acid or fumaric acid; b) an oligomeric or polymeric crosslinking agent containing vinyl ether-, vinyl ester- or (meth)acrylate-functional groups, with special preference being given to vinyl ether oligomers, for example divinyl ether-functionalised urethanes; c) the photoinitiator. The UV-curable powder coatings may also comprise white or coloured pigments. Accordingly, for example, there may preferably be used rutile titanium dioxide in concentrations of up to 50% by weight in order to obtain a cured powder coating with good hiding power. The process normally comprises electrostatic or tribostatic spraying of the powder onto the substrate, e.g. metal or wood, melting of the powder as a result of heating and, after a smooth film has been formed, radiation-curing of the coating using ultraviolet and/or visible light, for example using medium-pressure mercury lamps, metal halide lamps or xenon lamps. A particular advantage of radiation-curable powder coatings compared to corresponding thermally curable coatings is that the flow time after melting of the powder particles can be extended as desired in order to ensure the formation of a smooth high-gloss coating. In contrast to thermally curable systems, radiation-curable powder coatings can be formulated so that they melt at relatively low temperatures, without the undesirable effect of a reduction in shelf-life. For that reason they are also suitable as coatings for heat-sensitive substrates, for example wood or plastics. However, if the powder coatings are to be applied to non-heat-sensitive substrates, for example metals (vehicle coatings), it is also possible to make available "dual cure" powder coating formulations using the photoinitiators according to the invention. Such formulations will be known to the person skilled in the art; they are cured both thermally and also by means of UV and can be found in, for example, U.S. Pat. No. 5,922,473.

The compounds according to the invention may also be used in the form of an aqueous, for example 0.5 - 5%, preferably 0.5-2%, dispersion in polymer dispersions, for example in aqueous polyurethane dispersions, so-called PUDs.

The photocurable compositions according to the invention are suitable, for example, as coating substances for substrates of all kinds, e.g. wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which a protective layer or, by means of image-wise exposure, an image is to be applied.

The substrates can be coated by applying a liquid composition, a solution or a suspension or a powder to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents are, for example, ketones, ethers and esters, e.g. methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating methods, for example by printing methods such as flexography printing, lithography printing, inkjet, screen printing, spin-coating, immersion, roller application, knife coating, curtain pouring, brush application or spraying, especially by electrostatic spraying and reverse-roll coating, and also by electrophoretic deposition. It is also possible to apply the photosensitive layer to a temporary flexible support and then coat the final substrate by transferring the layer via lamination. Examples of types of application are to be found, for example, in Ullmann's Encyclopedia of Industrial Chemistry, 5th Ed., Vol. A18, pp. 491-500.

The amount applied (layer thickness) and the nature of the substrate (layer support) are dependent on the desired field of use.

A further field of use comprises compositions that are suitable for the coating of glass fibres, both for the inner and also for the middle and outer layers. The coated glass fibres may also be gathered into bundles giving a further coating. Such coating layers comprise UV-curable oligomers, UV-curable monomers and also at least one photoinitiator and additives.

Any UV-curable oligomer is suitable for the coating of glass fibres.

Further fields of use of photocuring are metal coating, for example the application of a finish to sheet metals and tubes, cans or bottle closures, and also photocuring on plastics coatings, for example PVC-based floor or wall coverings.

Examples of the photocuring of paper coatings are the application of a colourless finish to labels, packaging materials or book covers.

The photosensitivity of the compositions according to the invention usually extends from approximately 150 nm into the IR range. Suitable radiation is present, for example, in sunlight or light from artificial light sources. Accordingly a large number of the most varied kinds of light source may be used. Both point sources and planiform radiators (lamp arrays) are suitable. Examples are: carbon arc lamps, xenon arc lamps, medium-pressure, high-pressure and low-pressure mercury radiators doped, where appropriate, with metal halides (metal halide lamps), microwave-excited metal vapour lamps, excimer lamps, superactinic fluorescent tubes, fluorescent lamps, argon incandescent lamps, flash lamps, e.g. high-energy flash lamps, photographic floodlight lamps, light-emitting diodes (LED, OLED), electron beams and X-rays. The distance between the lamp and the substrate to be exposed may vary according to the intended use and the type and strength of the lamp and may be, for example, from 2 cm to 150 cm. Especially suitable are laser light sources, for example excimer lasers, such as Krypton-F lasers for exposure at 248 nm. Lasers in the visible and infrared or NIR range may also be used.

As already mentioned, curing according to the invention can be carried out solely by irradiation with electromagnetic radiation. Depending on the composition of the formulation to be cured, however, thermal curing before, during or after the irradiation is advantageous.

Thermal curing is carried out by methods known to the person skilled in the art. In general, the curing is carried out in an oven, e.g. a circulating air oven, on a heating plate or by irradiation with IR lamps. Unassisted curing at room temperature is also possible, depending on the binder system used. The curing temperatures are generally between room temperature and 150° C., for example from 25 to 150° C. or from 50 to 150° C. In the case of powder coatings or coil coatings, the curing temperatures may be even higher, e.g. up to 350° C.

The invention relates to the use of the photoinitiator compounds as described above as photoinitiators for the photopolymerization of compositions comprising compounds containing ethylenically unsaturated double bonds and to a process for the photopolymerization of monomeric, oligomeric or polymeric compounds containing at least one ethylenically unsaturated double bond, which comprises adding to the abovementioned compounds at least one photoinitiator as described above a photoinitiator mixture as described above and irradiating the resulting composition with electromagnetic radiation.

Interesting is the use of the composition as described above for producing pigmented and nonpigmented paints and varnishes, powder coatings, printing inks, printing plates, adhesives, pressure sensitive adhesives, dental compositions, gel coats, photoresists for electronics, electroplating resists, etch resists, both liquid and dry films, solder resists, resists to manufacture color filters for a variety of display applications, resists to generate structures in the manufacturing processes of plasma-display panels, electroluminescence displays and LCD, spacers for LCD, for holographic data storage (HDS), as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, as image recording material, for holographic recordings, microelectronic circuits, decolorizing materials, decolorizing materials for image recording materials, for image recording materials using microcapsules, as a photoresist material for a UV and visible laser direct imaging system, as a photoresist material used for forming dielectric layers in a sequential build-up layer of a printed circuit board; in particular the use of a photopolymerizable composition as described above for producing pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules.

Further of interest is a process as described above for producing pigmented and non-pigmented paints and varnishes, powder coatings, printing inks, printing plates, adhesives, pressure sensitive adhesives, dental compositions, gel coats, photoresists for electronics, electroplating resists, etch resists, both liquid and dry films, solder resists, resists to manufacture color filters for a variety of display applications, resists to generate structures in the manufacturing processes of plasma-display panels, electroluminescence displays and LCD, spacers for LCD, for holographic data storage (HDS), as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, as image recording material, for holographic recordings, microelectronic circuits, decolorizing materials, decolorizing materials for image recording materials, for image recording materials using microcapsules, as a photoresist material for a UV and visible laser direct imaging system, as a photoresist material used for forming dielectric layers in a sequential build-up layer of a printed circuit board; in particular a process for the preparation of pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules.

Preferred is a process as described above for the production of pigmented and non-pigmented surface coatings, overprint coatings, powder coatings, printing inks, inkjet inks, gel coats, composite materials or glass fibre coatings.

The invention relates also to a coated substrate which is coated on at least one surface with a composition as described above, as well as a polymerized or crosslinked composition obtained by curing a polymerizable composition as described above.

In particular of interest is the use of a composition as described above as a surface coating for food packaging materials, as well as a process as described above for the production of a surface coating for food packaging materials employing a composition as described above.

The examples which follow illustrate the invention in more detail, without restricting the scope to said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

PREPARATION EXAMPLES

For preparing the following examples starting materials as follow are employed:

As oxiranyl component (4-oxiranylmethoxy-phenyl)-phenyl-methanone is prepared from (4-hydroxy-phenyl)-phenyl-methanone and 2-chloromethyl-oxirane as taught by e.g. T. Nishikubo et al., Macromolecules 1998, 31, 2789-2796.

The polyether amines as listed below, purchased from HUNTSMAN (if not indicated otherwise):

Jeffamine D-230
($x\sim2.5$; MW ca. 230)

Jeffamine D-400
($x\sim6.1$; MW ca. 430)

Jeffamine ED-600
($y\sim9.0$, $[x+z]\sim3.6$; MW ca. 600)

Jeffamine EDR-148
($x = 2.0$; MW 148)

Jeffamine T-403
($[x+y+z]\sim5$-$6$; MW ca. 440)

Jeffamine EDR-176, ethylene glycol bis(3-aminopropyl) ether

Jeffamine EDR-104, 1,5-diamino-3-oxapentane

Additionally the following amines were reacted with (4-oxiranylmethoxy-phenyl)-phenyl-methanone (procedures are not optimized):

4,9-Dioxadodecane-1,12-diamine (7300-34-7)

4,7,10-Trioxatridecane-1,13-diamine (4246-51-9)

Polyethyleneimine MN 423 (Aldrich 468533; 29320-38-5); amine hydrogen equivalent weight AHEW (g amine/mol epoxide)=34.

Polyethyleneimine MW ca. 800 (Lupasol FG, provided by BASF SE; 9002-98-6); AHEW=35.6; primary amine/secondary amine/tertiary amine=1/0.9/0.5.

Polytetrahydrofuran amine MW ca. 400 (PolyTHFAmine 350, provided by BASF SE; 960525-56-8); AHEW=88; primary amine/secondary amine/tertiary amine=1/ 0.217/0.012.

Example 1

Ring-opening addition of 4-(oxiranylmethoxy-phenyl)-phenyl-methanone (4 eq) to hexane-1,6-diamine.

A mixture of (4-oxiranylmethoxy-phenyl)-phenyl-methanone (2.54 g, 0.01 mol) and hexane-1,6-diamine (16.8 meq N/g; 0.3 g, 5.0 mmol N) in n-propanol (15 ml) is stirred at 60° C. until epoxide conversion is complete (20 hours), the progress of the reaction being monitored by GLC. The solvent is then distilled off using a rotary evaporator to afford a slightly yellow resin (2.6 g).

LC/MS (pos. APCI), m/z (% area): found 1133.6 (≥80); calcd. 1132 ($C_{70}H_{58}N_2O_{12}$; title compound).

MS (pos. APCI), m/z: found 1133.6, 879.6, 624.4; calcd. 878 ($C_{54}H_{58}N_2O_9$; compound derived from threefold ring-opening addition), 624 ($C_{38}H_{44}N_2O_6$; compound derived from twofold ring-opening addition).

Example 2

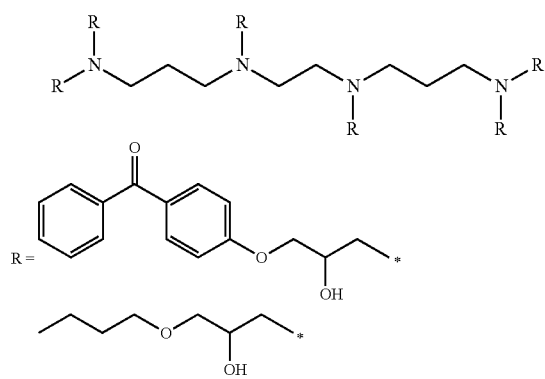

Ring-opening addition of 4-(oxiranylmethoxy-phenyl)-phenyl-methanone (4 eq) and 2-butoxymethyl-oxirane (2 eq) to N,N'-bis(3-aminopropyl)ethylenediamine.

A mixture of (4-oxiranylmethoxy-phenyl)-phenyl-methanone (2.54 g, 0.01 mol) and N,N'-bis(3-aminopropyl)ethylenediamine (22.2 meq N/g; 0.45 g, 10.0 mmol N) in n-propanol (15 ml) is stirred at 60° C. until epoxide conversion is complete (20 hours), the progress of the reaction being monitored by GLC. 2-Butoxymethyl-oxirane (95%; 0.68 g, 0.005 mol ) is added and the reaction mixture stirred at 60° C. for another 8 hours. The solvent is then distilled off using a rotary evaporator to afford a slightly yellow resin (3.8 g).

MS (pos. APCI), m/z (% relative intensity): found 1079.9 (40), 1203.8 (100), 1327.5 (80), 1451.6 (30); calcd. 1078 ($C_{59}H_{106}N_4O_{13}$; compound derived from single ring-opening addition of 4-(oxiranylmethoxy-phenyl)-phenyl-methanone and fivefold ring-opening addition of 2-butoxymethyl-oxirane), 1202 ($C_{68}H_{106}N_4O_{14}$; compound derived from twofold ring-opening addition of 4-(oxiranylmethoxy-phenyl)-phenyl-methanone and fourfold ring-opening addition of 2-butoxymethyl-oxirane), 1326 ($C_{77}H_{106}N_4O_{15}$; compound derived from threefold ring-opening addition of 4-(oxiranylmethoxy-phenyl)-phenyl-methanone and threefold ring-opening addition of 2-butoxymethyl-oxirane), 1450 ($C_{86}H_{106}N_4O_{16}$; compound derived from fourfold ring-opening addition of 4-(oxiranylmethoxy-phenyl)-phenyl-methanone and twofold ring-opening addition of 2-butoxymethyl-oxirane).

GPC (polystyrene calibrated; RI detector, THF), $M_n/M_w$/PDI (% area): 1164/1326/ 1.14 (96.3).

Example 3

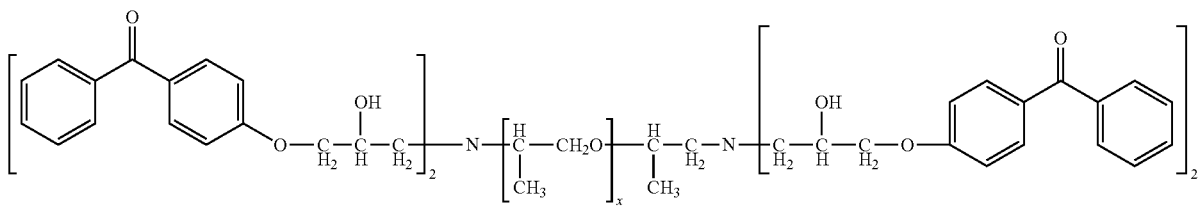

x~2.5

Ring-opening addition of 4-(oxiranylmethoxy-phenyl)-phenyl-methanone (4 eq) to Jeffamine D-230.

A mixture of (4-oxiranylmethoxy-phenyl)-phenyl-methanone (2.54 g, 0.01 mol) and Jeffamine D-230 (8.25 meq N/g; 0.6 g, 4.95 mmol N) in n-propanol (15 ml) is stirred at 60° C. until epoxide conversion is complete (20 hours), the progress of the reaction being monitored by GLC. The solvent is then distilled off using a rotary evaporator to afford a slightly yellow resin (3.15 g).

LC/MS (pos. APCI), m/z (% area): found 1207.6, 1265.6, 1323.6 (all three together ≥80); calcd. 1206 ($C_{73}H_{78}N_2O_{14}$; x=2), 1264 ($C_{76}H_{84}N_2O_{15}$; x=3), 1322 ($C_{79}H_{90}N_2O_{16}$; x=4).

GPC (polystyrene calibrated; RI detector, THF), $M_n/M_w$/PDI (% area): 1068/1164/ 1.09 (90.6).

Example 4

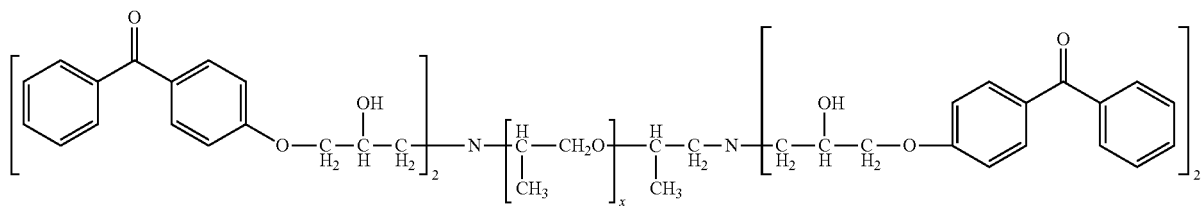

x~6.1

Ring-opening addition of 4-(oxiranylmethoxy-phenyl)-phenyl-methanone (4 eq) to Jeffamine D-400.

A mixture of (4-oxiranylmethoxy-phenyl)-phenyl-methanone (2.54 g, 0.01 mol) and Jeffamine D-400 (4.37 meq N/g; 1.14 g, 4.98 mmol N) in n-propanol (15 ml) is stirred at 60° C. until epoxide conversion is complete (20 hours), the progress of the reaction being monitored by GLC. The solvent is then distilled off using a rotary evaporator to afford a slightly yellow resin (3.65 g).

LC/MS (pos. APCI), m/z (% area): found 1207.6, 1265.6, 1323.7, 1381.7, 1439.7, 1497.8, 1555.8, 1613.8 (all three together ≥91); calcd. 1206 ($C_{73}H_{78}N_2O_{14}$; x=2), 1264 ($C_{76}H_{84}N_2O_{15}$; x=3), 1322 ($C_{79}H_{90}N_2O_{16}$; x=4), 1380 ($C_{82}H_{96}N_2O_{17}$; x=5), 1438 ($C_{85}H_{102}N_2O_{18}$; x=6), 1496 ($C_{88}H_{108}N_2O_{19}$; x=7), 1554 ($C_{91}H_{114}N_2O_{20}$; x=8), 1612 ($C_{94}H_{120}N_2O_{21}$; x=9).

GPC (polystyrene calibrated; RI detector, THF), $M_n/M_w$/PDI (% area): 383/1522/ 1.10 (89.4).

Example 5

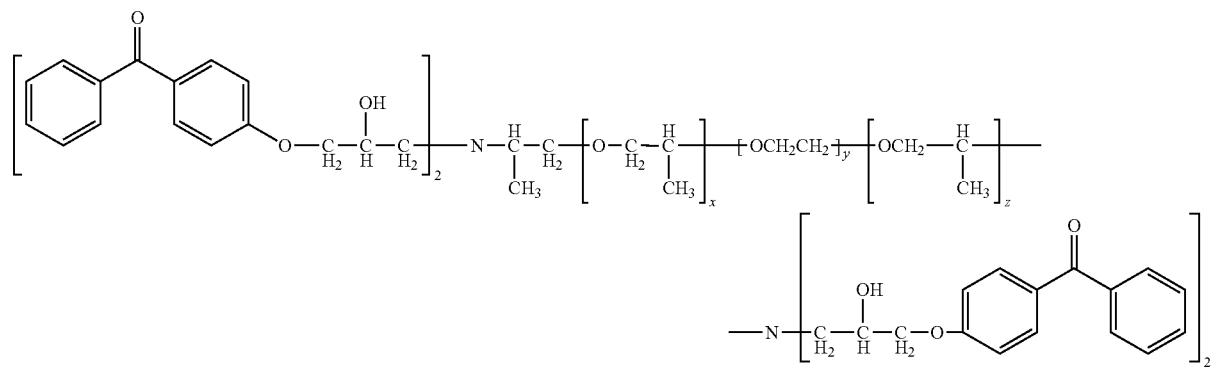

[x + z]~3.6, y~9

Ring-opening addition of 4-(oxiranylmethoxy-phenyl)-phenyl-methanone (4 eq) to Jeffamine ED-600.

A mixture of (4-oxiranylmethoxy-phenyl)-phenyl-methanone (2.54 g, 0.01 mol) and Jeffamine ED-600 (3.43 meq N/g; 1.46 g, 5.0 mmol N) in n-propanol (15 ml) is stirred at 60° C. until epoxide conversion is complete (20 hours), the progress of the reaction being monitored by GLC. The solvent is then distilled off using a rotary evaporator to afford a slightly yellow resin (3.85 g).

GPC (polystyrene calibrated; RI detector, THF), $M_n/M_w$/PDI (% area): 1491/1668/ 1.12 (91.3).

Example 6

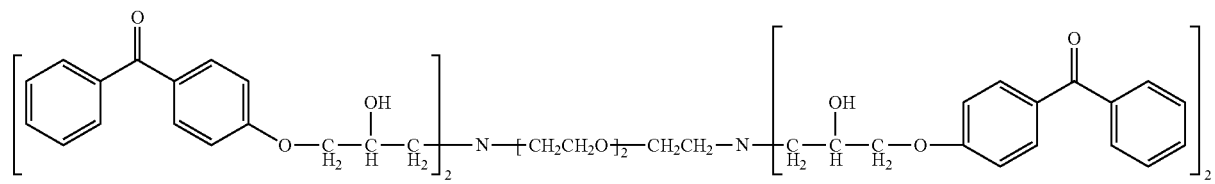

Ring-opening addition of 4-(oxiranylmethoxy-phenyl)-phenyl-methanone (4 eq) to Jeffamine EDR-148.

A mixture of (4-oxiranylmethoxy-phenyl)-phenyl-methanone (2.54 g, 0.01 mol) and Jeffamine EDR-148 (13.03 meq N/g; 0.38 g, 4.95 mmol N) in n-propanol/1,4-dioxane (15 ml/7 ml) is stirred at 70° C. until epoxide conversion is complete (20 hours), the progress of the reaction being monitored by GLC. The solvent is then distilled off using a rotary evaporator to afford a slightly yellow resin (3.1 g).

LC/MS (pos. APCI), m/z (% area): found 1165.6 (≥95); calcd. 1164 ($C_{70}H_{72}N_2O_{14}$; title compound).

MS (pos. APCI), m/z: found 1165.6, 911.4, 658.3; calcd. 910 ($C_{54}H_{58}N_2O_{11}$; compound derived from threefold ring-opening addition), 656 ($C_{38}H_{44}N_2O_8$; compound derived from twofold ring-opening addition).

Example 7

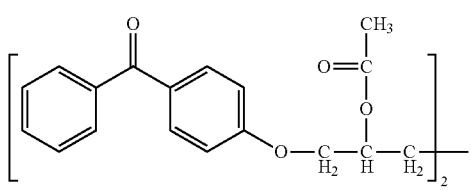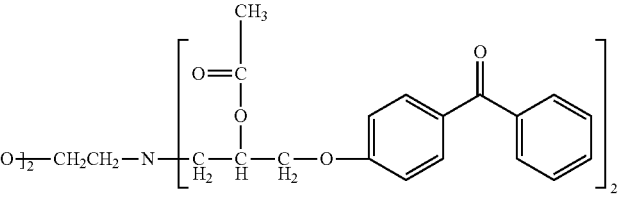

O-Acetylation of the compound of example 6.

The compound of example 6, newly prepared in the same manner as described above, is dissolved in chloroform (15 ml). Acetic anhydride (1.27 g, 12.4 mmol) is added and the mixture stirred at 70° C. during 20 hours, the progress of the reaction being monitored by GLC. The resulting solution is cooled down and sequentially washed with caustic soda (aqueous, 1 molar) and brine. The solvent is then distilled off using a rotary evaporator to afford a slightly yellow resin (3.4 g).

LC/MS (pos. APCI), m/z (% area): found 1333.8 (57), 1291.8 (28); calcd. 1332 ($C_{78}H_{80}N_2O_{18}$; title compound), 1290 ($C_{76}H_{78}N_2O_{17}$; compound derived from threefold O-acetylation).

Example 8

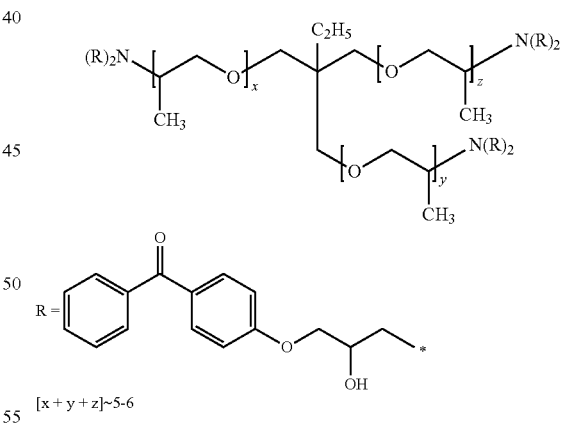

$[x+y+z]\sim 5\text{-}6$

Ring-opening addition of 4-(oxiranylmethoxy-phenyl)-phenyl-methanone (6 eq) to Jeffamine T-403.

A mixture of (4-oxiranylmethoxy-phenyl)-phenyl-methanone (3.81 g, 0.015 mol) and Jeffamine T-403 (6.0 meq N/g; 1.25 g, 7.5 mmol N) in n-propanol (20 ml) is stirred at 70° C. until epoxide conversion is complete (20 hours), the progress of the reaction being monitored by GLC. The solvent is then distilled off using a rotary evaporator to afford a slightly yellow resin (4.0 g).

GPC (polystyrene calibrated; RI detector, THF), $M_n/M_w/$PDI (% area): 1546/1799/ 1.16 (91.4).

Example 9

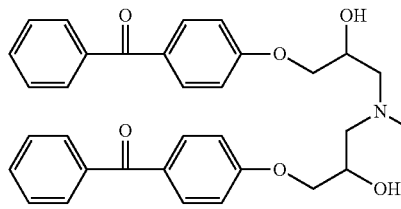 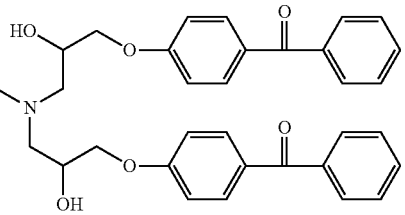

Ring-opening addition of 4-(oxiranylmethoxy-phenyl)-phenyl-methanone (4 eq) to 4,9-dioxadodecane-1,12-diamine.

4,9-Dioxadodecane-1,12-diamine (7300-34-7; 97%; 1.72 g, 8.17 mmol) is dissolved in a mixture of 1-propanol (50 ml) and 1,4-dioxane (23 ml). The resulting solution is stirred and brought to 40° C. (4-Oxiranylmethoxy-phenyl)-phenyl-methanone (8.58 g, 33.74 mmol) is added and the reaction mixture stirred overnight at 72° C. Volatiles are then removed on a rotary evaporator and the residue dried on an oil pump to afford the title compound (10.7 g).

LC/MS (pos. APCI), m/z (% area): found 1221.6 (86.1), 255.1 (4.3); calcd. 1220 ($C_{74}H_{80}ON_2O_{14}$; title compound), 254 ($C_{16}H_{14}O_3$; (4-oxiranylmethoxy-phenyl)-phenyl-methanone).

The product (10.7 g) is mixed with Sartomer® $SR_{344}$ [polyethylene glycol ($PEG_{400}$) diacrylate—CAS 26570-48-9] (2.5 g) and Irgastab® UV22 (0.1 g) [4-benzylidene-2,6-di-tert-butyl-cyclohexa-2,5-dienone] using dichloromethane (20 g) as auxiliary solvent to afford, after removal of the solvent, a reduced viscosity-sample (13.4 g) which is subjected to testing (i.e. determination of cure speed).

The photoinitiator concentration as determined by weight is equivalent to 53.4% w/w (4-methoxy-phenyl)-phenyl-methanone.

Example 10

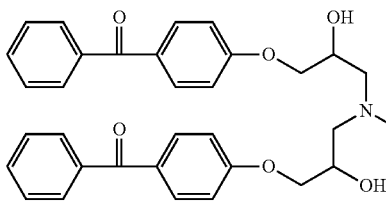 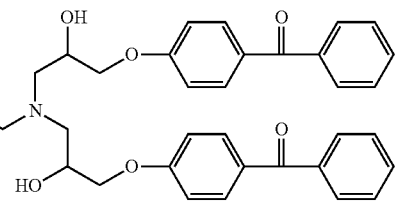

Ring-opening addition of 4-(oxiranylmethoxy-phenyl)-phenyl-methanone (4 eq) to 4,7,10-trioxatridecane-1,13-diamine. 4,7,10-Trioxatridecane-1,13-diamine (4246-51-9; 98%; 1.82 g, 8.10 mmol) is dissolved in a mixture of 1-propanol (50 ml) and 1,4-dioxane (23 ml). The resulting solution is stirred and brought to 40° C. (4-Oxiranylmethoxy-phenyl)-phenyl-methanone (8.40 g, 33.03 mmol) is added and the reaction mixture stirred overnight at 72° C. Volatiles are then removed on a rotary evaporator and the residue dried on an oil pump to afford the title compound (10.7 g).

LC/MS (pos. APCI), m/z (% area): found 1237.5 (85.4), 255.0 (6.7); calcd. 1236 ($C_{74}H_{80}N_2O_{15}$; title compound), 254 ($C_{16}H_{14}O_3$; (4-oxiranylmethoxy-phenyl)-phenyl-methanone).

The product (10.7 g) is mixed with Sartomer SR344 (provided by Sartomer company) (1.79 g) and Irgastab® UV22 (provided by BASF SE) (0.1 g) using dichloromethane (20 g) as auxiliary solvent to afford, after removal of the solvent, a reduced viscosity-sample (12.5 g) which is subjected to testing (i.e. determination of cure speed).

The photoinitiator concentration as determined by weight is equivalent to 56.1% w/w (4-methoxy-phenyl)-phenyl-methanone.

Example 11

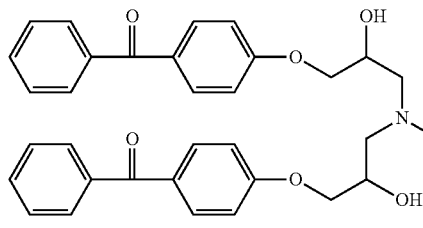
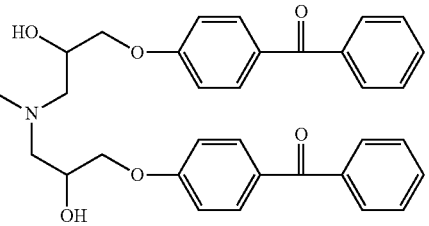

Ring-opening addition of 4-(oxiranylmethoxy-phenyl)-phenyl-methanone (4 eq) to ethylene glycol bis(3-aminopropyl) ether (Jeffamine EDR-176).

Ethylene glycol bis(3-aminopropyl) ether (Jeffamine EDR-176, 2997-01-5; 98%; 1.51 g, 8.40 mmol) is dissolved in a mixture of 1-propanol (50 ml) and 1,4-dioxane (23 ml). The resulting solution is stirred and brought to 40° C. (4-Oxiranylmethoxy-phenyl)-phenyl-methanone (8.72 g, 34.29 mmol) is added and the reaction mixture stirred overnight at 72° C. Volatiles are then removed on a rotary evaporator and the residue dried on an oil pump to afford the title compound (10.8 g).

LC/MS (pos. APCI), m/z (% area): found 1193.5 (90.9), 255.0 (3.1); calcd. 1192 ($C_{72}H_{76}N_2O_{14}$; title compound), 254 ($C_{16}H_{14}O_3$; (4-oxiranylmethoxy-phenyl)-phenyl-methanone).

The product (10.8 g) is mixed with Sartomer SR344 (2.53 g) and Irgastab® UV22 (0.1 g) using dichloromethane (20 g) as auxiliary solvent to afford, after removal of the solvent, a reduced viscosity-sample (13.4 g) which is subjected to testing (i.e. determination of cure speed).

The photoinitiator concentration as determined by weight is equivalent to 54.3% w/w (4-methoxy-phenyl)-phenyl-methanone.

Example 12

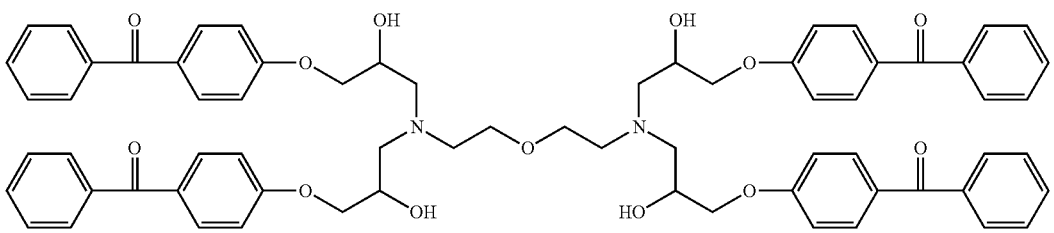 [SMILES: O=C(c1ccccc1)c1ccc(OCC(O)CN(CCOCCN(CC(O)COc2ccc(C(=O)c3ccccc3)cc2)CC(O)COc2ccc(C(=O)c3ccccc3)cc2)CC(O)COc2ccc(C(=O)c3ccccc3)cc2)cc1]

Ring-opening addition of 4-(oxiranylmethoxy-phenyl)-phenyl-methanone (4 eq) to 1,5-diamino-3-oxapentane (Jeffamine EDR-104).

1,5-Diamino-3-oxapentane (Jeffamine EDR-104, 2752-17-2; 95%; 0.98 g, 8.94 mmol) is dissolved in a mixture of 1-propanol (50 ml) and 1,4-dioxane (23 ml). The resulting solution is stirred and brought to 40° C. (4-Oxiranylmethoxy-phenyl)-phenyl-methanone (9.57 g, 37.63 mmol) is added and the reaction mixture stirred overnight at 72° C. Volatiles are then removed on a rotary evaporator and the residue dried on an oil pump to afford the title compound (11.22 g).

LC/MS (pos. APCI), m/z (% area): found 1121.4 (87.2), 255.0 (5.4); calcd. 1120 ($C_{68}H_{68}N_2O_{13}$; title compound), 254 ($C_{16}H_{14}O_3$; (4-oxiranylmethoxy-phenyl)-phenyl-methanone).

The product (11.22 g) is mixed with Sartomer $SR_{344}$ (2.53 g) and Irgastab® UV22 (0.1 g) using dichloromethane (20 g) as auxiliary solvent to afford, after removal of the solvent, a reduced viscosity-sample (13.2 g) which is subjected to testing (i.e. determination of cure speed).

The photoinitiator concentration as determined by weight is equivalent to 60.5% w/w (4-methoxy-phenyl)-phenyl-methanone.

Example 13

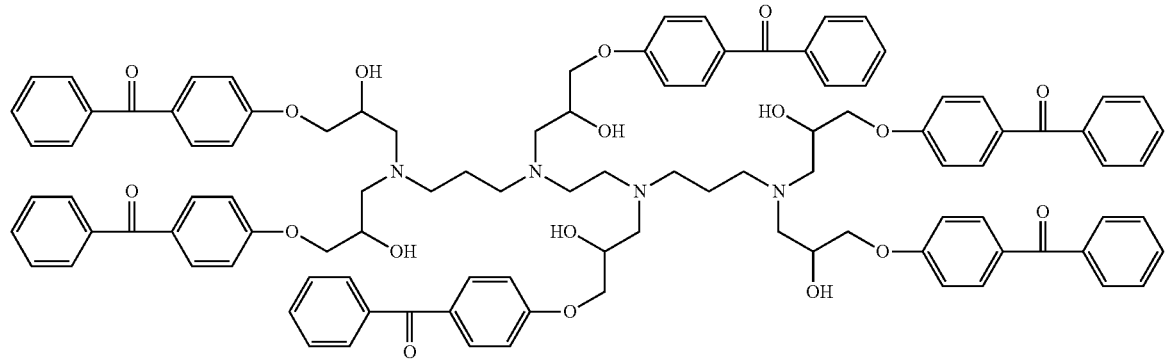 [SMILES: O=C(c1ccccc1)c1ccc(OCC(O)CN(CCCN(CC(O)COc2ccc(C(=O)c3ccccc3)cc2)CC(O)COc2ccc(C(=O)c3ccccc3)cc2)CCN(CCCN(CC(O)COc2ccc(C(=O)c3ccccc3)cc2)CC(O)COc2ccc(C(=O)c3ccccc3)cc2)CC(O)COc2ccc(C(=O)c3ccccc3)cc2)cc1]

Ring-opening addition of 4-(oxiranylmethoxy-phenyl)-phenyl-methanone (6 eq) to N,N'-bis(3-aminopropyl)ethylenediamine (similar to example 2).

N,N'-Bis(3-aminopropyl)ethylenediamine (22.2 meq N/g; 1.06 g, 23.53 mmol N) is dissolved in a mixture of 1-propanol (50 ml) and 1,4-dioxane (23 ml). The resulting solution is stirred and brought to 40° C. (4-Oxiranylmethoxy-phenyl)-phenyl-methanone (9.07 g, 35.67 mmol) is added and the reaction mixture stirred overnight at 72° C. Volatiles are then removed on a rotary evaporator and the residue dried on an oil pump to afford the title compound (10.75 g).

MS (pos. ESI), m/z (% intensity): found 1700.48 (30); calcd. 1698 ($C_{104}H_{106}N_4O_{18}$; title compound).

The product (10.75 g) is mixed with Sartomer SR344 (2.53 g) and Irgastab® UV22 (0.1 g) using dichloromethane (20 g) as auxiliary solvent to afford, after removal of the solvent, a reduced viscosity-sample (13.2 g) which is subjected to testing (i.e. determination of cure speed).

The photoinitiator concentration as determined by weight is equivalent to 57.3% w/w (4-methoxy-phenyl)-phenyl-methanone.

Example 14

Ring-opening addition of 4-(oxiranylmethoxy-phenyl)-phenyl-methanone [(60 mol % based on amine hydrogen equivalent weight (AHEW)) and 1,2-epoxybutane (40 mol % based on AHEW) to polyethyleneimine MN 423 (Aldrich 468533; 29320-38-5). Polyethyleneimine MN 423 (Aldrich 468533, 29320-38-5; amine hydrogen equivalent weight AHEW (g amine/mol epoxide)=34; 1.58 g, equivalent to 46.47 mmol epoxide) is dissolved in a mixture of 1-propanol (50 ml) and 1,4-dioxane (23 ml). The resulting solution is stirred and brought to 40° C. (4-Oxiranylmethoxy-phenyl)-phenyl-methanone (99%; 7.15 g, 27.84 mmol; 60mol% based on AHEW) is added and the reaction mixture stirred at 60° C. during 24 hours. 1,2-Epoxybutane (1.34 g, 18.58 mmol; 40mol % based on AHEW) is added and the reaction mixture stirred another 24 hours at 60° C. Additional 1,2-Epoxybutane (1.34 g, 18.58 mmol; 40 mol % based on AHEW) is then added and the reaction mixture stirred another 42 hours at 60° C. Volatiles are then removed on a rotary evaporator and the residue dried on an oil pump to afford the title compound (10.63 g).

$M_w$ (calcd.): ca. 2-680; GPC (polystyrene calibrated; RI detector, THF), $M_n/M_w$/PDI (% area): 1'003/1'366/1.36 (94.6); %w/w residual (4-oxiranylmethoxy-phenyl)-phenyl-methanone: <0.5 (by LC); glass transition temperature ($T_g$): 37.2° C.

The product (10.63 g) is mixed with Sartomer $SR_{344}$ (2.53 g) and Irgastab® UV22 (0.1 g) using tetrahydrofuran (20 g) as auxiliary solvent to afford, after removal of the solvent, a reduced viscosity-sample (12.4 g) which is subjected to testing (i.e. determination of cure speed).

The photoinitiator concentration as determined by weight is equivalent to 47.7% w/w (4-methoxy-phenyl)-phenyl-methanone.

Example 15

Ring-opening addition of 4-(oxiranylmethoxy-phenyl)-phenyl-methanone (60 mol % based on AHEW) and 1,2-epoxybutane (40 mol % based on AHEW) to polyethyleneimine MW ca. 800 (Lupasol FG, BASF; 9002-98-6).

Polyethyleneimine MW ca. 800 (Lupasol FG, BASF, 9002-98-6; AHEW=35.6; primary amine/secondary amine/tertiary amine=1/0.9/0.5; 1.64 g, equivalent to 46.07 mmol epoxide) is dissolved in a mixture of 1-propanol (50 ml) and 1,4-dioxane (23 ml). The resulting solution is stirred and brought to 40° C. (4-Oxiranylmethoxyphenyl)-phenyl-methanone (99%; 7.10 g, 27.64 mmol; 60 mol % based on AHEW) is added and the reaction mixture stirred at 60° C. during 24 hours. 1,2-Epoxybutane (1.33 g, 18.44 mmol; 40 mol % based on AHEW) is added and the reaction mixture stirred another 24 hours at 60° C. Additional 1,2-Epoxybutane (1.33 g, 18.44 mmol; 40 mol % based on AHEW) is then added and the reaction mixture stirred another 42 hours at 60° C. Volatiles are then removed on a rotary evaporator and the residue dried on an oil pump to afford the title compound (10.33 g).

$M_w$ (calcd.): ca. 4-877; GPC (polystyrene calibrated; RI detector, THF), $M_n/M_w$/PDI (% area): 1'286/2'068/1.61 (93.8); %w/w residual (4-oxiranylmethoxy-phenyl)-phenyl-methanone: <0.5 (by LC); glass transition temperature ($T_g$): 40.3° C.

The product (10.33 g) is mixed with Sartomer SR344 (2.53 g) and Irgastab® UV22 (0.1 g) using tetrahydrofuran (20 g) as auxiliary solvent to afford, after removal of the solvent, a reduced viscosity-sample (12.4 g) which is subjected to testing (i.e. determination of cure speed).

The photoinitiator concentration as determined by weight is equivalent to 47.3% w/w (4-methoxy-phenyl)-phenyl-methanone.

Example 16

Ring-opening addition of 4-(oxiranylmethoxy-phenyl)-phenyl-methanone (90 mol % based on AHEW) and 1,2- epoxybutane (10 mol % based on AHEW) to polytetrahydrofuran amine MW ca. 400 (PolyTHFAmine 350, BASF; 960525-56-8). Polytetrahydrofuran amine MW ca. 400 (PolyTHFAmine 350, BASF, 960525-56-8; AHEW=88; primary amine/secondary amine/tertiary amine=1/0.217/0.012; 2.72 g, equivalent to 30.91 mmol epoxide) is dissolved in a mixture of 1-propanol (50 ml) and 1,4-dioxane (23 ml). The resulting solution is stirred and brought to 40° C. (4-Oxiranylmethoxy-phenyl)-phenyl-methanone (99%; 7.13 g, 27.76 mmol; 90 mol % based on AHEW) is added and the reaction mixture stirred at 60° C. during 24 hours. 1,2-Epoxybutane (0.44 g, 6.1 mmol; 20 mol % based on AHEW) is added and the reaction mixture stirred another 48 hours at 60° C. Volatiles are then removed on a rotary evaporator and the residue dried on an oil pump to afford the title compound (10.84 g).

$M_w$ (calcd.): ca. 1-473; GPC (polystyrene calibrated; RI detector, THF), $M_n/M_w$/PDI (% area): 1'322/1'755/1.33 (96.5); % w/w residual (4-oxiranylmethoxy-phenyl)-phenyl-methanone: <0.5 (by LC).

The photoinitiator concentration as determined by weight is equivalent to 54.3% w/w (4-methoxy-phenyl)-phenyl-methanone.

Example 17

Ring-opening addition of 4-(oxiranylmethoxy-phenyl)-phenyl-methanone (90 mol % based on AHEW) and 1,2-epoxybutane (10 mol % based on AHEW) to polytetrahydrofuran amine MW ca. 400 (PolyTHFAmine 350, BASF; 960525-56-8).

Polytetrahydrofuran amine MW ca. 400 (PolyTHFAmine 350, BASF, 960525-56-8; AHEW=88; primary amine/secondary amine/tertiary amine=1/0.217/0.012; 2.72 g, equivalent to 30.91 mmol epoxide) is dissolved in a mixture of 1-propanol (50 ml) and 1,4-dioxane (23 ml). The resulting solution is stirred and brought to 40° C. (4-Oxiranylmethoxy-phenyl)-phenyl-methanone (99%; 7.13 g, 27.76 mmol; 90 mol % based on AHEW) is added and the reaction mixture stirred at 60° C. during 24 hours. 1,2-Epoxybutane (0.22 g, 3.05 mmol; 10 mol % based on AHEW) is added and the reaction mixture stirred another 48 hours at 60° C. Volatiles are then removed on a rotary evaporator and the residue dried on an oil pump to afford a yellowish resin (10.7 g). The resin is re-dissolved in a mixture of 1-propanol (50 ml) and 1,4-dioxane (23 ml). 1,2-Epoxybutane (0.22 g, 3.05 mmol; 10 mol % based on AHEW) is added and the reaction mixture stirred another 48 hours at 60° C. Volatiles are then removed on a rotary evaporator and the residue dried on an oil pump to afford the title compound (10.69 g).

$M_w$ (calcd.): ca. 1-473; GPC (polystyrene calibrated; RI detector, THF), $M_n/M_w$/PDI (% area): 1-313/1-754/1.34 (94.3); % w/w residual (4-oxiranylmethoxy-phenyl)-phenyl-methanone: <0.5 (by LC).

The product (10.69 g) is mixed with Sartomer $SR_{344}$ (0.53 g) and Irgastab® UV22 (0.03 g) using tetrahydrofuran (20 g) as auxiliary solvent to afford, after removal of the solvent, a reduced viscosity-sample (10.4 g) which is subjected to testing (i.e. determination of cure speed).

The photoinitiator concentration as determined by weight is equivalent to 56.7% w/w (4-methoxy-phenyl)-phenyl-methanone.

Example 18

Ring-opening addition of 4-(oxiranylmethoxy-phenyl)-phenyl-methanone (100 mol % based on AHEW) to polytetrahydrofuran amine MW ca. 400 (PolyTHFAmine 350, BASF; 960525-56-8).

Polytetrahydrofuran amine MW ca. 400 (PolyTHFAmine 350, BASF, 960525-56-8; AHEW=88; primary amine/secondary amine/tertiary amine=1/0.217/0.012; 2.57 g, equivalent to 29.2 mmol epoxide) is dissolved in a mixture of 1-propanol (50 ml) and 1,4-dioxane (23 ml). The resulting solution is stirred and brought to 40° C. (4-Oxiranylmethoxy-phenyl)-phenyl-methanone (99%; 7.50 g, 29.2 mmol; 100 mol % based on AHEW) is added and the reaction mixture stirred at 60° C. during 42 hours. Additional (4-oxiranylmethoxy-phenyl)-phenyl-methanone (0.23 g, 0.90 mmol; 3 mol % based on AHEW) is added and the reaction mixture stirred another 48 hours at 60° C. Volatiles are then removed on a rotary evaporator and the residue dried on an oil pump to afford the title compound (10.7 g).

$M_w$ (calcd.): 1'556; GPC (polystyrene calibrated; RI detector, THF), $M_n/M_w$/PDI (% area): 1'453/1'838/1.27 (93.9); %w/w residual (4-oxiranylmethoxy-phenyl)-phenyl-methanone: 1.2 (by LC).

The product (10.7 g) is mixed with Sartomer $SR_{344}$ (1.12 g) and Irgastab® UV22 (0.06 g) using tetrahydrofuran (20 g) as auxiliary solvent to afford, after removal of the solvent, a reduced viscosity-sample (11.6 g) which is subjected to testing (i.e. determination of cure speed).

The photoinitiator concentration as determined by weight is equivalent to 55.1% w/w (4-methoxy-phenyl)-phenyl-methanone.

APPLICATION EXAMPLES

Ink-Formulation 1 is prepared by mixing the following components:
15.0 wt-% of a hexafunctional polyester acrylate (EBECRYL 450, provided by Cytec)
20.0 wt-% of a tetrafunctional polyester acrylate (EBECRYL 812, provided by Cytec)
15.0 wt-% of an amine modified polyether acrylate (EBECRYL 83, provided by Cytec)
33.3 wt-% of a monofunctional acrtylate (EBECRYL 160, provided by Cytec)
0.7 wt-% of a silicone additive (DC 57), provided by DOW Corning;
16.0 wt-% of Blue Pigment (IRGALITE Blue GLO, provided by BASF SE)
Testing of Formulations A-H
Formulations A-H are prepared by mixing 95% of formulation 1 with 1% of (Irgacure® 369, =2-benzyl-2-(dimethylamino)-1-[4-(4-morpholinyl)phenyl]-1-butanone provided by BASF SE) and 4% of the compound to be tested. The formulations and corresponding test compounds are given in the following table 1:

TABLE 1

| Formulation | comprises compound of example |
|---|---|
| A | 2 |
| B | 1 |
| C | 5 |
| D | 4 |
| E | 3 |
| F | 6 |
| G | 7 |
| H | 8 |

Formulations are applied using a Prüfbau machine onto a corona treated PEC (poly-ethylene carbonate) white foil (1.6 g/m² transferred). Samples are exposed to a medium pressure mercury lamp (200 W/cm) using an aluminium reflector under air at different belt speeds: polymerization efficiency is assessed using the transfer test immediately after the irradiation. In this, the printed side is covered by a white paper substrate (Lumiart brilliant, couché standard, 135 gm²) and further submitted to a pressure of 200 N applied by an aluminium cylinder (transfer speed of 1 m/min). The visible transfer of the ink from the exposed surface to the paper characterizes a poor curing of the ink surface.

Reactivity is measured by the cure speed defined as the maximum belt speed required to achieve proper cure (no ink transfer) at a constant light intensity.

The results are collected in the following table 2.

TABLE 2

| Formulation | Cure speed (m/min) |
|---|---|
| A | 65 |
| B | 75 |
| C | 65 |
| D | 60 |
| E | 70 |
| F | 80 |
| G | 60 |
| H | 65 |

Testing of Formulations J-S

Formulations J-S are prepared by mixing 94% of formulation 1 with 1% of (Irgacure® 369, provided by BASF SE) and 5% of the photoinitiator compound to be tested.

The formulations are applied onto a corona treated PEC white foil using a Prüfbau machine (1.4-1.6 g/m² transferred) at 25° C. with a pressure of 500N. The substrate is printed with a conveyer speed of 1 m/min.

The printed substrate is exposed to a medium pressure mercury lamp (200 W/cm) using a cold mirror reflector under air at appropriate belt speeds for each sample. Polymerization efficiency is assessed using the transfer test immediately after the irradiation. In this, the printed side is covered by a white paper substrate (Lumiart brilliant, couché standard, 135 gm²) and further submitted to a pressure of 200 N applied by an aluminum cylinder (transfer speed of 1 m/min). Optimal surface curing condition is achieved when the white paper surface in contact with the printed sample is free from any trace of transferred ink. Reactivity is measured by the cure speed defined as the maximum belt speed required for getting proper cure (=no ink transfer) at a constant light intensity.

The formulations and corresponding test results are given in the following table 3:

TABLE 3

| Formulation | Compound of example | Cure speed (m/min) |
|---|---|---|
| J | 9 | 50 |
| K | 10 | 50 |
| L | 11 | 50 |
| M | 12 | 45 |
| N | 13 | 50 |
| O | 14 | 45 |
| P | 15 | 45 |
| Q | 16 | 55 |
| R | 17 | 55 |
| S | 18 | 55 |

The invention claimed is:

1. A photoinitiator compound comprising a photoactive moiety Q and an amine functionality, the photoinitiator compound represented by formula (1)

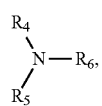

wherein
$R_4$ and $R_5$ are a photoactive moiety Q;
$R_6$ is linear or branched $C_1$-$C_{20}$alkyl which optionally is substituted by one or more identical or different $Y_2$;
or is linear or branched $C_2$-$C_{20}$alkyl which is interrupted by one or more identical or different $Y_1$ and which interrupted $C_2$-$C_{20}$alkyl optionally is substituted by one or more identical or different $Y_2$;
or is a group E-$R_9$ or $E_1$-$R_{13}$;
Q is a photoactive moiety

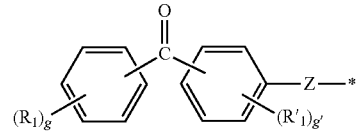

wherein the asterisk (*) denotes the bonding to the N atom;
g and g' are 0;
$R_1$ and $R'_1$ independently of each other are hydrogen, linear or branched $C_1$-$C_6$alkyl, $OC_1$-$C_3$alkyl, $OR_3$, $NO_2$, CN, (CO)$OR_2$ or halogen;
Z is a group

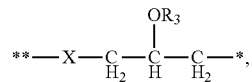

wherein the double asterisk (**) denotes the bonding to the phenyl ring and the asterisk (*) denotes the bonding to the nitrogen atom;
X is O;
$R_2$ is hydrogen or $C_1$-$C_6$alkyl;
$R_3$ is hydrogen or (CO)CH$_3$;
$Y_1$ is O or $NR_{16}$;
$Y_2$ is $N(R_{10})(R_{11})$;
$R_9$ is $G_2$-$N(R_{10})(R_{11})$ or hydrogen;
$R_{10}$ and $R_{11}$ independently of each other are a photoactive moiety Q, hydrogen,
or $R_{10}$ and $R_{11}$ are linear or branched $C_2$-$C_{18}$alkyl which is interrupted by one or more O and which interrupted $C_2$-$C_{18}$alkyl optionally is substituted by $OR_{12}$;
$R_{12}$ is hydrogen;
$R_{13}$ is $N(R_{10})(R_{11})$;
$R_{16}$ is a photoactive moiety Q, hydrogen, or linear or branched $C_2$-$C_{18}$alkyl which is interrupted by one or more O and which interrupted $C_2$-$C_{18}$alkyl optionally is substituted by $OR_{12}$ or $NR_{10}R_{11}$;
E is a group

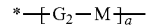

wherein the asterisk (*) denotes the bond to the N-atom;
$G_2$ in the multiple occurring moieties $*-\!\!+\!G_2-M\!+\!\!_a-$ are identical or different and are linear or branched $C_2$-$C_6$alkylene;
a in the multiple occurring moieties $*-\!\!+\!G_2-M\!+\!\!_a-$ independently are an integer 1-50;
M in the multiple occurring moieties $*-\!\!+\!G_2-M\!+\!\!_a-$, $-\!\!+\!G_3-M\!+\!\!_b-$, $-\!\!+\!G_3-M\!+\!\!_c-$ or
$-\!\!+\!G_3-M\!+\!\!_d-$ are identical or different and are O or $N(R_{16})$;
$E_1$ is a group

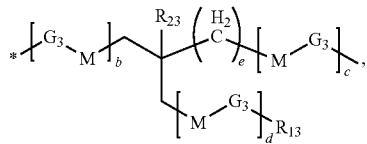

wherein the asterisk (*) denotes the bond to the N-atom;

e is 1;
$G_3$ in the multiple occurring moieties $-\!\!+\!G_3-M\!+\!\!_b-$, $-\!\!+\!G_3-M\!+\!\!_c-$ or $-\!\!+\!G_3-M\!+\!\!_d-$ are identical or different and are linear or branched $C_2$-$C_6$alkylene;
the sum of b+c+d is an integer 1-12; and
$R_{23}$ is linear or branched $C_1$-$C_6$alkyl.

2. A photoinitiator mixture comprising more than one of the photoinitiator compounds as defined in claim 1.

3. A photopolymerizable composition comprising
(A) at least one ethylenically unsaturated photopolymerizable compound and
(B) at least one photoinitiator according to claim 1.

4. A photopolymerizable composition according to claim 3, which additionally to the component (B) comprises at least one further photoinitiator (C) and/or other customary additives (D).

5. A polymerizable composition according to claim 3, which comprises 0.05 to 15% by weight of the photoinitiator compound or photoinitiator mixture based on the total composition.

6. A coated substrate coated on at least one surface with a composition according to claim 3.

7. A polymerized or crosslinked composition obtained by curing a polymerizable composition according to claim 3.

* * * * *